(12) United States Patent
Pasloske et al.

(10) Patent No.: US 7,033,749 B2
(45) Date of Patent: *Apr. 25, 2006

(54) RIBONUCLEASE RESISTANT RNA PREPARATION AND UTILIZATION

(75) Inventors: Brittan L. Pasloske, Austin, TX (US); Dwight B. DuBois, Austin, TX (US); David M. Brown, Austin, TX (US); Matthew M. Winkler, Austin, TX (US)

(73) Assignees: Ambion, Inc., Austin, TX (US); Cenetron Diagnostics LLC, Cedar Creek, TX (US)

( * ) Notice: Subject to any disclaimer, the term of this patent is extended or adjusted under 35 U.S.C. 154(b) by 362 days.

This patent is subject to a terminal disclaimer.

(21) Appl. No.: 10/120,013

(22) Filed: Apr. 10, 2002

(65) Prior Publication Data

US 2002/0192689 A1 Dec. 19, 2002

Related U.S. Application Data

(63) Continuation of application No. 09/665,638, filed on Sep. 19, 2000, now Pat. No. 6,399,307, which is a continuation of application No. 09/282,054, filed on Mar. 30, 1999, now Pat. No. 6,214,982, which is a continuation of application No. 08/881,571, filed on Jun. 24, 1997, now Pat. No. 5,939,262, which is a continuation-in-part of application No. 08/675,153, filed on Jul. 3, 1996, now Pat. No. 5,677,124.

(60) Provisional application No. 60/021,145, filed on Jul. 3, 1996.

(51) Int. Cl.
*C12Q 1/70* (2006.01)
*C12Q 1/68* (2006.01)
*C12N 7/00* (2006.01)
*C07H 21/02* (2006.01)
*C07H 21/04* (2006.01)

(52) U.S. Cl. ............... 435/5; 435/6; 435/235.1; 536/23.1; 536/23.5; 536/23.52

(58) Field of Classification Search ............ 435/6, 435/91.1, 235.1; 536/23.1, 24.1
See application file for complete search history.

(56) References Cited

U.S. PATENT DOCUMENTS

| | | | |
|---|---|---|---|
| 5,091,309 A | 2/1992 | Schlesinger et al. ....... 435/69.1 |
| 5,443,969 A | 8/1995 | Wilson et al. ........... 435/91.32 |
| 5,500,360 A | 3/1996 | Ahlquist et al. ............ 435/468 |
| 5,578,473 A | 11/1996 | Palese et al. ........... 435/235.1 |
| 5,589,367 A | 12/1996 | Donson et al. .......... 435/320.1 |
| 5,602,242 A | 2/1997 | Ahlquist et al. ......... 536/23.72 |
| 5,614,413 A | 3/1997 | Morrow ..................... 435/427 |
| 5,618,699 A | 4/1997 | Hamamoto et al. ........ 435/69.7 |
| 5,622,705 A | 4/1997 | Morrow ................... 424/199.1 |
| 5,627,060 A | 5/1997 | Ahlquist et al. ............ 800/278 |
| 5,677,124 A * | 10/1997 | DuBois et al. ................. 435/5 |
| 5,716,821 A | 2/1998 | Wertz et al. ............. 435/235.1 |
| 5,736,388 A * | 4/1998 | Chada et al. ............ 435/320.1 |
| 5,739,026 A | 4/1998 | Garoff et al. ............... 435/352 |
| 5,766,840 A * | 6/1998 | Kim et al. ..................... 435/5 |
| 5,919,625 A * | 7/1999 | DuBois et al. ................. 435/6 |
| 5,939,262 A * | 8/1999 | Pasloske et al. ............... 435/6 |
| 6,214,982 B1 * | 4/2001 | Pasloske et al. .......... 536/23.1 |
| 6,399,307 B1 * | 6/2002 | Pasloske et al. ............... 435/6 |
| 6,613,749 B1 * | 9/2003 | Forstova et al. ............. 514/44 |

FOREIGN PATENT DOCUMENTS

| | | |
|---|---|---|
| EP | 0278667 A2 | 8/1988 |
| EP | 0 525 882 | 2/1993 |
| EP | 0278667 B1 | 7/1994 |
| WO | WO 87/06261 | 10/1987 |
| WO | WO 93/03161 | 2/1993 |
| WO | WO 94/28171 | 12/1994 |
| WO | WO 95/02067 | 1/1995 |
| WO | WO 95/14109 | 5/1995 |
| WO | WO 95/15974 | 6/1995 |
| WO | WO 95/34684 | 12/1995 |
| WO | WO 00/63440 | 10/2000 |

OTHER PUBLICATIONS

Lim et al., Tranlational repression and specific RNA binding by the coat protein of the Pseudomonas phage PP7. The Journal of Biological Chemistry, vol. 276, No. 25, pp. 22507-22513, 2001.*

Wu et al., A comparison of two phage coat protein-RNA interactions. Nucleic Acids Research, vol. 16, No. 11, pp. 5055-5066, 1988.*

Beckett et al., Roles of operator and non-operator RNA sequences in bacteriophage R17 capsid assembly. Journal of Molecular Biology, vol. 204, pp. 939-947, 1988.*

(Continued)

*Primary Examiner*—Terry McKelvey
*Assistant Examiner*—Jennifer Dunston
(74) *Attorney, Agent, or Firm*—Fulbright & Jaworski LLP

(57) ABSTRACT

The present invention relates to nuclease resistant nucleic acids in general and ribonuclease resistant RNAs in particular. Methods of making and using such nucleic acids are disclosed.

34 Claims, 2 Drawing Sheets

OTHER PUBLICATIONS

GenBank Accession No. L09130, 1982.*

Rao et al., DNA packaging of bacteriophage T4 proheads in vitro: Evidence that prohead expansion is not coupled to DNA packaging. Journal of Molecular Biology, vol. 185, No. 3, pp. 565-578, 1985.*

Wickner et al., Membrane-associated assembly of M13 phage in extracts of virus-infected *Escherichia coli*. PNAS, USA, vol. 74, No. 2, pp. 505-509, 1977.*

Gottlieb et al., In vitro packaging of the bacteriophage phi6 ssRNA genomic precursors. Virology, vol. 181, pp. 589-594, 1991.*

Turner et al., The tobacco mosaic virus assembly origin RNA. Functional characteristics defined by directed mutagenesis. Journal of Molecular Biology, vol. 203, No. 3, pp. 531-547, 1988.*

Bradley, Ultrastructure of bacteriophages and bacteriocins, Bacteriological Reviews, vol. 31, No. 4, pp. 230-314, 1967.*

Conry et al., "Characterization of a Messenger RNA Polynucleotide Vaccine Vector," *Cancer Research*, 55(7): 1397-1400, Apr. 1995.

Dwarki, Malone and Verma, "Cationic Liposome-Mediated RNA Transfection," *Methods in Enzymology*, 217:644-654, 1993.

Heidenreich, Pieken and Eckstein, "Chemically Modified RNA: Approaches and Applications," *FASEB J.*, 7:90-96, 1993.

Natarajan et al., "An Internally Controlled Virion PCR for the Measurement of HIV-1 RNA in Plasma," *PCR Methods Appl.*,3(6):346-350, 1994.

Peabody, "The RNA binding site of bacteriophage MS2 coat protein," *The EMBO Journal* 12(2):595-600, 1993.

Reischl and Kochanowski., "Quantitative PCR: A Survey of the Present Technology," *Molecular Biotechnology*,3:55-71, 1995.

Stockley et al., "Molecular Mechanism of RNA Phage Morphogenesis," *Int. J. Biochem.*, 26(10/11)1249-1260, 1994.

Stonehouse and Stockley, "Effects of Amino Acid Substitution on the Thermal Stability of MS2 Capsids Lacking Genomic RNA," *FEBS*, 334(3):355-389, Nov. 1993.

Argetsinger and Gussin, "Intact Ribonucleic Acid from Defective Particles of Bacteriophage R17," *J Mol Biol*, 21:421-434, 1966.

Aslanzadeh et al., "Evaluation of PCR and Nested PCR for Laboratory Diagnosis of Hepatitis C Virus Infection," *Mol Cell Probes*, 10:173-178, 1996.

Barlow et al., "Analysis and Genotyping of PCR Products of the Amplicor HIV-1 Kit," *J Virological Methods*, 52:65-74, 1995.

Collins et al., "Preparation and Characterization of RNA Standards for Use in Quantitative Branched DNA Hybridization Assays," *Analytical Biochemistry*, 226:120-129, 1995.

Dolja et al., "Phylogeny of Capsid Proteins of Rod-Shaped and Filamentous RNA Plant Viruses: Two Families with Distinct Patterns of Sequence and Probably Structure Conservation," *Virology*, 184:79-86, 1991.

Duda et al., "Expression of Plasmid-Encoded Structural Proteins Permits Engineering of Bacteriophage T4 Assembly," *Virology*, 179:728-737, 1990.

Durham, "Structures and Roles of the Polymorphic Forms of Tobacco Mosaic Virus Protein," *J. Mol. Biol.*, 67:289-305, 1972.

Durham, "The Cause of Irreversible Polymerisation of Tobacco Mosaic Virus Protein," *FEBS Letters*, 25(1):147-152, 1972.

Fritsch et al., "Specificity of TMV RNA Encapsidation: in vitro Coating of Heterologous RNA by TMV Protein," *Virology*, 56:33-45, 1973.

Gallie et al., "In Vivo Uncoating and Efficient Expression of Foreign mRNAs Packaged in TMV-Like Particles," *Science*, 236:1122-1124, 1987.

Gallie et al., "The Effect of Multiple Dispersed Copies of the Origin-of-Assembly Sequence From TMV RNA on the Morphology of Pseudovirus Particles Assembled In Vitro," *Virology*, 158:473-476, 1987.

Gal-On et al., "Nucleotide Sequence of the Zucchini Yellow Mosaic Virus Capsid-Encoding Gene and its Expression in *Escherichia coli*," Gene 87:273-277, 1990.

Gibbs, "Tobamovirus Group," *C.M.I./A.A.B. Descriptions of Plant Viruses*, No. 184, Commonwealth Bureaux and the Association of Applied Biologists, Sep. 1977.

Goelet et al., "Nucleotide Sequence of Tobacco Mosaic Virus RNA," *Proc. Natl. Acad. Sci. USA*, 79:5818-5922, 1982.

Golmohammadi et al., "The Refined Structure of Bacteriophage MS2 at 2·8 Å Resolution," *J Mol Biol*, 234:620-639, 1993.

Goulden et al., "Structure of Tobraviral Particles: A Model Suggested From Sequence Conservation in Tobraviral and Tobamoviral Coat Proteins," *J. Mol. Biol.*, 227:1-8, 1992.

Guilley et al., "Observations Concerning the Sequence of Two Additional Specifically Encapsidated RNA Fragments Originating From the Tobacco-Mosaic-Virus Coat-Protein Cistron," *Eur. J. Biochem.*, 54:145-153, 1975.

Guilley et al., "Sequence of a Specifically Encapsidated RNA Fragment Originating From the Tobacco-Mosaic-Virus Coat-Protein Cistron," *Eur. J. Biochem.*, 54:135-144, 1975.

Guo et al., "sRNA of Phage φ29 of *Bacillus subtilis* Mediates DNA Packaging of φ29 Proheads Assembled in *Escherichia coli*," Virology, 185:395-400, 1991.

Harrison, "Pea Early-Browning Virus," *C.M.I./A.A. B. Descriptions of Plant Viruses*, No. 120, Commonwealth Bureaux and the Association of Applied Biologists, Jul. 1973.

Harrison, "Tobacco Rattle Virus," *C.M.I./A.A.B. Descriptions of Plant Viruses*, No. 12, Commonwealth Bureaux and the Association of Applied Biologists, Jun. 1970.

Haynes et al., "Development of a Genetically-Engineered, Candidate Polio Vaccine Employing the Self-Assembling Properties of the Tobacco Mosaic Virus Coat Protein," *Biotechnology*, 4:637-641, 1986.

Heisenberg, "Formation of Defective Bacteriophage Particles by fr *Amber* Mutants," *J. Mol. Biol.*, 17:136-144, 1966.

Hughes and Andrew, "Creation of Deletion, Insertion and Substitution Mutations Using a Single Pair of Primers and PCR," *Biotechniques*, 20(2):188-196, 1996.

Hwang et al., "Expression of Tobacco Mosaic Virus Coat Protein and Assembly of Pseudovirus Particles in *Escherichia coli*," *Proc. Natl. Acad. Sci. USA*, 91:9067-9071, 1994.

International Search Report dated Oct. 21, 1997 (AMBI: 036P) PCT/US97/12551.

Jagadish et al., "Expression of Potyvirus Coat Protein in *Escherichia coli* and Yeast and its Assembly into Virus-Like Particles," *Journal of General Virology*, 72:1543-1550, 1991.

Jupin et al., "Direct Recovery of in vitro Transcripts in a Protected Form Suitable for Prolonged Storage and Shipment at Ambient Temperatures," *Nucleic Acids Research*, 17(2):815, 1989.

Koenig and Lesemann, "Potexvirus Group," *C.M.I./A.A.B. Descriptions of Plant Viruses*, No. 200, Commonwealth Bureaux and the Association of Applied Biologists, Aug. 1978.

LeCuyer et al., "Mutants of the Bacteriophage MS2 Coat Protein that Alter its Cooperative Binding," *Biochem*, 34: 10600-10606, 1995.

Lim and Peabody, "Mutations that Increase the Affinity of a Translational Repressor for RNA," *Nuc Acids Res*, 22(18): 3748-3752, 1994.

Lim et al., "Altering the RNA Binding Specificity of a Translational Repressor," *J Biol Chem*, 269(12):9006-9010, Mar. 1994.

Lu and Andrieu, "Use of the Human Immunodeficiency Virus Virion as a Universal Standard for Viral RNA Quantitation by Reverse Transcription-Linked Polymerase Chain Reaction," *J Infect Diseases*, 167:1499-1500, 1993.

Mastico et al., "Multiple Presentation of Foreign Peptides on the Surface of an RNA-Free Sphereical Bacteriophage Capside," *J General Virology*, 74:541-548, 1993.

Mellors et al., "Prognosis in HIV-1 Infection Predicted by the Quantity of Virus in Plasma," *Science*, 272:1167-1170, May 1996.

Meshi et al., "Nucleotide Sequence of a Cloned cDNA Copy of TMV (Cowpea Strain) RNA, Including the Assembly Origin, the Coat Protein Cistron, and the 3' Non-Coding Region," *Mol. Gen. Genet.*, 184:20-25, 1981.

Mulder et al., "Rapid and Simple PCR Assay for Quantitation of Human Immunodeficiency Virus Type 1 RNA in Plasma: Application to Acute Retroviral Infection," *J Clin Microbiol*, 32(2):292-300, Feb. 1994.

Olkkonen et al., "In Vitro Assembly of Infectious Nucleocapsids of Bacteriophage φ6: Formation of a Recombinant Double-Stranded RNA Virus," *Proc. Natl. Acad. Sci. USA*, 87:9173-9177, 1990.

Pachl et al., "Rapid and Precise Quantification of HIV-1 RNA in Plasma Using a Branched DNA Signal Amplification Assay," *J Acquired Immune Deficiency Syndromes and Human Retrovirology*, 8:446-454, 1995.

Peabody and Ely, "Control of Translational Repression by Protein—Protein Interactions," *Nuc Acids Res*, 20(7):1649-1655, 1992.

Peabody and Lim, "Complementation of RNA Binding Site Mutations in MS2 Coat Protein Heterodimers," *Nuc Acids Res*, 24(12):2352-2359, 1996.

Peabody, "Translational Repression by Bacteriophage MS2 Coat Protein Expressed from a Plasmid," *J Biol Chem*, 265(10):5684-5689, Apr. 1990.

Piatak et al., "Quantitative Competitive Polymerase Chain Reaction for Accurate Quantitation of HIV DNA and RNA Species," *Biotechniques*, 14(1):70-79, 1993.

Pickett and Peabody, "Encapsidation of Heterologous RNAs by Bacteriophage MS2 Coat Protein," *Nuc Acids Res*, 21 (19):4621-4626, 1993.

Pushko et al., "Analysis of RNA Phage *fr* Coat Protein Assembly by Insertion, Deletion and Substitution Mutagenesis," *Protein Engineering*, 6(8):883-891, 1993.

Qiao et al., "Interference with Bacteriophage φ6 Genomic RNA Packaging by Hairpin Structures," *J Virology*, 69(9): 5502-5505, Sep. 1995.

Rochon and Siegel, "Chloroplast DNA Transcripts Are Encapsidated by Tobacco Mosaic Virus Coat Protein," *Proc. Natl. Acad. Sci. USA*, 81:1719-1723, 1984.

Rochon et al., "Encapsidation of 18 S rRNA by Tobacco Mosaic Virus Coat Protein," *Virology*, 150:140-148, 1986.

Rosenberg and Studier, "T7 RNA Polymerase Can Direct Expression of Influenza Virus Cap-Binding Protein (PB2) in *Escherichia coli*," *Gene*, 59:191-200, 1987.

Sacher et al., "Hybrid Brome Mosaic Virus RNAs Express and Are Packaged in Tobacco Mosaic Virus Coat Protein in vivo," *Virology*, 167:15-24, 1988.

Schein, "Production of Soluble Recombinant Proteins in Bacteria," *Biotechnology*, 7:1141-1149, 1989.

Schneeberger and Zeillinger, "PCR-Mediated Synthesis of Exogenous Competitors for Quantitative RT-PCR," *Biotechniques*, 20(3):360-361, 1996.

Shaklee et al., "Infectious Positive- and Negative-Strand Transcript RNAs from Bacteriophage Qβ cDNA Clone," *Virology*, 163:209-213, 1988.

Shaklee, "Negative-Strand RNA Replication by Qβ and MS2 Positive-Strand RNA Phage Replicases," *Virology*, 178:340-343, 1990.

Shiba and Saigo, "Packaging of tRNA and 6 S Stable RNA into Bacteriophage MS2 Particles Produced in *Escherichia coli* Treated with 5-Fluorouracil," *Virology*, 119:209-213, 1982.

Shiba and Suzuki, "Localization of a Protein in the RNA-A Protein Complex of RNA Phage MS2," *Biochimica et Biophysica Acta*, 654:249-255, 1981.

Shire et al., "Preparation and Properties of Recombinant DNA Derived Tobacco Mosaic Virus Coat Protein," *Biochemistry*, 29:5119-5126, 1990.

Siegel, "Pseudovirions of Tobacco Mosaic Virus," *Virology*, 46:50-59, 1971.

Sleat et al., "Packaging of Recombinant RNA Molecules into Pseudovirus Particles Directed by the Origin-of-Assembly Sequence From Tobacco Mosaic Virus RNA," *Virology*, 155:299-308, 1986.

Sleat et al., "Selective Recovery of Foreign Gene Transcripts as Virus-Like Particles in TMV-Infected Transgenic Tobaccos," *Nucleic Acids Research*, 16(8):3127-3141, 1988.

Stockley et al., "Probing Sequence-Specific RNA Recognition by the Bacteriophage MS2 Coat Protein," *Nuc Acids Res*, 23(13):2512-2518, 1995.

Studier et al., "Use of T7 RNA Polymerase to Direct Expression of Cloned Genes," *Methods in Enzymology*, 185:60-89, 1990.

Sugiyama, "Tobacco Mosaic Viruslike Rods Formed by "Mixed Reconstitution" Between MS2 Ribonucleic Acid and Tobacco Mosaic Virus Protein," *Virology*, 28(3):488-492, 1966.

Turner and Butler, "Essential Features of the Assembly Origin of Tobacco Mosaic Virus RNA as Studied by Directed Mutagenesis," *Nucleic Acids Research*, 14(23): 9229-9242, 1986.

Turner et al., "Assembly of Hybrid RNAs with Tobacco Mosaic Virus Coat Protein. Evidence for Incorporation of Disks in 5'-Elongation Along the Major RNA Tail," *J. Mol. Biol.*, 209:407-422, 1989.

Valegard et al., "Crystal Structure of an RNA Bacteriophage Coat Protein-Operator Complex," *Nature*, 371:623-626, Oct. 1994.

Valegard et al., "The Three-dimensional Structure of the Bacterial Virus MS2," *Nature*, 345:36-41, May 1990.

van Gemen, "A One-Tube Quantitative HIV-1 RNA NASBA Nucleic Acid Amplification Assay Using Electrochemiluminescent (ECL) Labelled Probes," *J Viorological Methods*, 49:157-168, 1994.

Wilson et al., "Effects of the 5'-Leader Sequence of Tobacco Mosaic Virus RNA, or Derivatives Thereof, on Foreign mRNA and Native Viral Gene Expression," *NATO ASI Series, Post-Transcriptional Control of Gene Expression*, vol. H49, McCarthy, J.E.G. and Tuite, M.F., eds., Springer-Verlag, Berlin, Heidelberg, pp. 261-275, 1990.

Witherell et al., "Specific Interaction Between RNA Phage Coat Proteins and RNA," *Proc Nuc Acid Res Molec Biol*, 40:185-220, 1991.

Witherell et al., "Cooperative Binding of R17 Coat Protein to RNA," *Biochem*, 29:11051-11057, 1990.

Young et al., "Detection of Hepatitis C Virus RNA by a Combined Reverse Transcription-Polymerase Chain Reaction Essay," *J Clinical Microbiol*, 31(4):882-886, Apr. 1993.

Zimmern and Hunter, "Point Mutation in the 30-K Open Reading Frame of TMV Implicated in Temperature-Sensitive Assembly and Local Lesion Spreading of Mutant Ni 2519," *The EMBO Journal*, 2(11):1893-1900, 1983.

Zimmern, "An Extended Secondary Structure Model For The Tmv Assembly Origin, And Its Correlation With Protection Studies And An Assembly Defective Mutant," *The Embo Journal*, 2(11):1901-1907, 1983.

Zimmern, "The 5' End Group of Tobacco Mosaic Virus RNA is $m^7G^{5'}$ $ppp^{5'}$ Gp," *Nucleic Acids Research*, 2(7): 1189-1201, 1975.

* cited by examiner

```
                            SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 1:

CCTTTCGGGG TCCTGCTCAA CTT                                                23

(2) INFORMATION FOR SEQ ID NO: 2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 2:

GATTAGATCT GAGTTGAACT TCTTTGTTGT CTTC                                    34

(2) INFORMATION FOR SEQ ID NO: 3:

(i) SEQUENCE CHARACTERISTICS:
        (A) LENGTH: 1718 base pairs
        (B) TYPE: nucleic acid
        (C) STRANDEDNESS: single
        (D) TOPOLOGY: linear (xi) SEQUENCE DESCRIPTION: SEQ ID NO: 3:

CCATGGCTAT CGCTGTAGGT AGCCGGAATT CCATTCCTAG GAGGTTTGAC CTGTGCGAGC        60

TTTTAGTACC CTTGATAGGG AGAACGAGAC CTTCGTCCCC TCCGTTCGCG TTTACGCGGA       120

CGGTGAGACT GAAGATAACT CATTCTCTTT AAAATATCGT TCGAACTGGA CTCCCGGTCG       180

TTTTAACTCG ACTGGGGCCA AAACGAAACA GTGGCACTAC CCCTCTCCGT ATTCACGGGG       240

GGCGTTAAGT GTCACATCGA TAGATCAAGG TGCCTACAAG CGAAGTGGGT CATCGTGGGG       300

TCGCCCGTAC GAGGAGAAAG CCGGTTTCGG CTTCTCCCTC GACGCACGCT CCTGCTACAG       360

CCTCTTCCCT GTAAGCCAAA ACTTGACTTA CATCGAAGTG CCGCAGAACG TTGCGAACCG       420

GGCGTCGACC GAAGTCCTGC AAAAGGTCAC CCAGGGTAAT TTTAACCTTG GTGTTGCTTT       480

AGCAGAGGCC AGGTCGACAG CCTCACAACT CGCGACGCAA ACCATTGCGC TCGTGAAGGC       540

GTACACTGCC GCTCGTCGCG GTAATTGGCG CCAGGCGCTC CGCTACCTTG CCCTAAACGA       600

AGATCGAAAG TTTCGATCAA AACACGTGGC CGGCAGGTGG TTGGAGTTGC AGTTCGGTTG       660

GTTACCACTA ATGAGTGATA TCCAGGGTGC ATATGAGATG CTTACGAAGG TTCACCTTCA       720

AGAGTTTCTT CCTATGAGAG CCGTACGTCA GGTCGGTACT AACATCAAGT TAGATGGCCG       780

TCTGTCGTAT CCAGCTGCAA ACTTCCAGAC AACGTGCAAC ATATCGCGAC GTATCGTGAT       840

ATGGTTTTAC ATAAACGATG CACGTTTGGC ATGGTTGTCG TCTCTAGGTA TCTTGAACCC       900

ACTAGGTATA GTGTGGGAAA AGGTGCCTTT CTCATTCGTT GTCGACTGGC TCCTACCTGT       960
```

-continued

```
AGGTAACATG CTCGAGGGCC TTACGGCCCC CGTGGGATGC TCCTACATGT CAGGAACAGT    1020

TACTGACGTA ATAACGGGTG AGTCCATCAT AAGCGTTGAC GCTCCCTACG GGTGGACTGT    1080

GGAGAGACAG GGCACTGCTA AGGCCCAAAT CTCAGCCATG CATCGAGGGG TACAATCCGT    1140

ATGGCCAACA ACTGGCGCGT ACGTAAAGTC TCCTTTCTCG ATGGTCCATA CCTTAGATGC    1200

GTTAGCATTA ATCAGGCAAC GGCTCTCTAG ATAGAGCCCT CAACCGGAGT TTGAAGCATG    1260

GCTTCTAACT TTACTCAGTT CGTTCTCGTC GACAATGGCG GAACTGGCGA CGTGACTGTC    1320

GCCCCAAGCA ACTTCGCTAA CGGGGTCGCT GAATGGATCA GCTCTAACTC GCGTTCACAG    1380

GCTTACAAAG TAACCTGTAG CGTTCGTCAG AGCTCTGCGC AGAATCGCAA ATACACCATC    1440

AAAGTCGAGG TGCCTAAAGT GGCAACCCAG ACTGTTGGTG GTGTAGAGCT TCCTGTAGCC    1500

GCATGGCGTT CGTACTTAAA TATGGAACTA ACCATTCCAA TTTTCGCTAC GAATTCCGAC    1560

TGCGAGCTTA TTGTTAAGGC AATGCAAGGT CTCCTAAAAG ATGGAAACCC GATTCCCTCA    1620

GCAATCGCAG CAAACTCCGG CATCTACTAA TAGACGCCGG CCATTCAAAC ATGAGGATTA    1680

CCCATGTCGA AGACAACAAA GAAGTTCAAC TCAGATCT                            1718

(2) INFORMATION FOR SEQ ID NO: 4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 4:

GATTGGTACC TGCTATGTCA GTTCCCCTTG GTTCTCT                              37

(2) INFORMATION FOR SEQ ID NO: 5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 5:

GATTAGATCT AAGTTGGAGG ACATCAAGCA GCCATGCAAA T                         41

(2) INFORMATION FOR SEQ ID NO: 6:

(i) SEQUENCE CHARACTERISTICS:
        (A) LENGTH: 1867 base pairs
        (B) TYPE: nucleic acid
        (C) STRANDEDNESS: single
        (D) TOPOLOGY: linear (xi) SEQUENCE DESCRIPTION: SEQ ID NO: 6:

CCATGGCTAT CGCTGTAGGT AGCCGGAATT CCATTCCTAG GAGGTTTGAC CTGTGCGAGC      60

TTTTAGTACC CTTGATAGGG AGAACGAGAC CTTCGTCCCC TCCGTTCGCG TTTACGCGGA     120

CGGTGAGACT GAAGATAACT CATTCTCTTT AAAATATCGT TCGAACTGGA CTCCCGGTCG     180

TTTTAACTCG ACTGGGGCCA AAACGAAACA GTGGCACTAC CCCTCTCCGT ATTCACGGGG     240

GGCGTTAAGT GTCACATCGA TAGATCAAGG TGCCTACAAG CGAAGTGGGT CATCGTGGGG     300

TCGCCCGTAC GAGGAGAAAG CCGGTTTCGG CTTCTCCCTC GACGCACGCT CCTGCTACAG     360

CCTCTTCCCT GTAAGCCAAA ACTTGACTTA CATCGAAGTG CCGCAGAACG TTGCGAACCG     420

GGCGTCGACC GAAGTCCTGC AAAAGGTCAC CCAGGGTAAT TTTAACCTTG GTGTTGCTTT     480
```

```
AGCAGAGGCC AGGTCGACAG CCTCACAACT CGCGACGCAA ACCATTGCGC TCGTGAAGGC      540

GTACACTGCC GCTCGTCGCG GTAATTGGCG CCAGGCGCTC CGCTACCTTG CCCTAAACGA      600

AGATCGAAAG TTTCGATCAA AACACGTGGC CGGCAGGTGG TTGGAGTTGC AGTTCGGTTG      660

GTTACCACTA ATGAGTGATA TCCAGGGTGC ATATGAGATG CTTACGAAGG TTCACCTTCA      720

AGAGTTTCTT CCTATGAGAG CCGTACGTCA GGTCGGTACT AACATCAAGT TAGATGGCCG      780

TCTGTCGTAT CCAGCTGCAA ACTTCCAGAC AACGTGCAAC ATATCGCGAC GTATCGTGAT      840

ATGGTTTTAC ATAAACGATG CACGTTTGGC ATGGTTGTCG TCTCTAGGTA TCTTGAACCC      900

ACTAGGTATA GTGTGGGAAA AGGTGCCTTT CTCATTCGTT GTCGACTGGC TCCTACCTGT      960

AGGTAACATG CTCGAGGGCC TTACGGCCCC CGTGGGATGC TCCTACATGT CAGGAACAGT     1020

TACTGACGTA ATAACGGGTG AGTCCATCAT AAGCGTTGAC GCTCCCTACG GGTGGACTGT     1080

GGAGAGACAG GGCACTGCTA AGGCCCAAAT CTCAGCCATG CATCGAGGGG TACAATCCGT     1140

ATGGCCAACA ACTGGCGCGT ACGTAAAGTC TCCTTTCTCG ATGGTCCATA CCTTAGATGC     1200

GTTAGCATTA ATCAGGCAAC GGCTCTCTAG ATAGAGCCCT CAACCGGAGT TTGAAGCATG     1260

GCTTCTAACT TTACTCAGTT CGTTCTCGTC GACAATGGCG GAACTGGCGA CGTGACTGTC     1320

GCCCCAAGCA ACTTCGCTAA CGGGGTCGCT GAATGGATCA GCTCTAACTC GCGTTCACAG     1380

GCTTACAAAG TAACCTGTAG CGTTCGTCAG AGCTCTGCGC AGAATCGCAA ATACACCATC     1440

AAAGTCGAGG TGCCTAAAGT GGCAACCCAG ACTGTTGGTG GTGTAGAGCT TCCTGTAGCC     1500

GCATGGCGTT CGTACTTAAA TATGGAACTA ACCATTCCAA TTTTCGCTAC GAATTCCGAC     1560

TGCGAGCTTA TTGTTAAGGC AATGCAAGGT CTCCTAAAAG ATGGAAACCC GATTCCCTCA     1620

GCAATCGCAG CAAACTCCGG CATCTACTAA TAGACGCCGG CCATTCAAAC ATGAGGATTA     1680

CCCATGTCGA AGACAACAAA GAAGTTCAAC TCAGATCTAA GTTGGAGGAC ATCAAGCAGC     1740

CATGCAAATG TTAAAACATA GCACTATAGA ACTCTGCAAG CCTCGAGTGA GAGTGCATCC     1800

AGTGCATGCA GGGCCTATTG CACCAGGCCA GATGAGAGAA CCAAGGGGAA CTGACATAGC     1860

AGGTACC                                                              1867

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 7:

GCAGAAAGCG TCTAGCCATG GCGT                                             24

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 8:

CTCGCAAGCA CCCTATCAGG CAGT                                             24
```

RIBONUCLEASE RESISTANT RNA PREPARATION AND UTILIZATION

BACKGROUND OF THE INVENTION

This application is a continuation of application Ser. No. 09/665,638 filed Sep. 19, 2000, now issued as U.S. Pat. No. 6,399,307, which is a continuation of Ser. No. 09/282,054 filed Mar. 30, 1999, now issued as U.S. Pat. No. 6,214,982, which is a continuation of Ser. No. 08/881,571 filed Jun. 24, 1997, now issued as U.S. Pat. No. 5,939,262 on Aug. 17, 1999, which is a continuation-in-part of Ser. No. 08/675,153 filed Jul. 3, 1996, now issued as U.S. Pat. No. 5,677,124 on Oct. 14, 1997, and provisional application Ser. No. 60/021,145 filed Jul. 3, 1996.

In the last few years, diagnostic assays and assays for specific mRNA species have been developed based on the detection of specific nucleic acid sequences. These assays depend on such technologies as RT-PCR™ (Mulder, 1994), isothermal amplification (NASBA) (Van Gemen, 1994), and branched chain DNA (Pachl, 1995). Many of these assays have been adapted to determine the absolute concentration of a specific RNA species. These absolute quantification assays require the use of an RNA standard of which the precise amount has been previously determined. These RNA standards are usually synthesized by in vitro transcription or are the infectious agents themselves. The RNA is purified and then quantified by several different methods, such as absorbance at $OD_{260}$, phosphate analysis, hyperchromicity or isotopic tracer analysis is (Collins, 1995).

Quantifying virus RNA sequences in plasma is an important tool for assessing the viral load in patients with, for example, Human Immunodeficiency Virus (HIV), Hepatitis C Virus (HCV), and other viruses such as HTLV-1, HTLV-2, hepatitis G, enterovirus, dengue fever virus, and rabies. Viral load is a measure of the total quantity of viral particles within a given .patient at one point in time. In chronic infections viral load is a function of a highly dynamic equilibrium of viral replication and immune-mediated host clearance. The benefits of determining viral load include the ability to: 1) assess the degree of viral replication at the time of diagnosis—an estimate having prognostic implications, 2) monitor the effect of antiviral medications early in the disease course, and 3) quickly assess the effects of changing antiviral medications.

Presently, the most sensitive method available for HIV quantification in plasma employs PCR™. There are 4 major steps involved in PCR™ analysis of HIV: 1) Sample preparation, 2) Reverse transcription, 3) Amplification, and 4) Detection. Variability in any of these steps will affect the final result. An accurate quantitative assay requires that each step is strongly controlled for variation. In the more rigorous PCR™ assay formats, a naked RNA standard is added to the denaturant just prior to the isolation of the viral RNA from plasma (Mulder, 1994). A less precise method is to add the standard to the viral RNA after it has been purified (Piatak, 1993). It is important that the RNA standards are precisely calibrated and that they withstand the rigors of the assay procedures.

There is a need for ribonuclease resistant RNA standards. RNA is susceptible to environmental ribonucleases. Producing ribonuclease-free reagents is non-trivial. A danger in using naked RNA as a standard for quantification is its susceptibility to ribonuclease digestion. Compromised standards generate inaccurate values. This problem can be compounded in clinical laboratory settings where the personnel are not usually trained in RNA handling. These factors introduce doubt as to the validity of the data generated.

Naked RNA standards are very susceptible to ribonuclease digestion. Some RNA based assays have been formatted so that users access an RNA standard tube only once and then discard it to minimize the possibility of contaminating the RNA standard with ribonucleases. However, the standards are aliquoted into microfuge tubes which are not guaranteed to be ribonuclease-free introducing another potential source for contamination. As well, there is a short period of time during which the RNA is exposed to a pipette tip before it is placed in the denaturing solution. If the pipette tip is contaminated with ribonuclease then the RNA standard will be degraded and the assay compromised. Another disadvantage of using naked RNA standards are that they must be stored frozen. In the branched DNA HIV assay formatted by Chiron Corp., the potential for RNA degradation is so risky that their assays include single stranded DNA instead of RNA for their standard (Pachl, 1995). The DNA is calibrated against RNA. The DNA standard is much less likely to be degraded. Thus, there is a need for RNA standards which are resistant to ribonucleases and in which there is no doubt about the integrity of the standard. These standards would also be more convenient if they did not need to be stored frozen so that they could be used immediately, no thawing required.

Those of skill know how to bring about chemical alteration of RNA. Such alterations can be made to nucleotides prior to their incorporation into RNA or to RNA after it has been formed. Ribose modification (Piecken 1991) and phosphate modification (Black, 1972) have been shown to enhance RNA stability in the presence of nucleases. Modifications of the 2' hydroxyl and internucleotide phosphate confers nuclease resistance by altering chemical groups that are necessary for the degradation mechanism employed by ribonucleases (Heidenreich, 1993). While such chemical modification can confer ribonuclease resistance, there is no known suggestion in the art that such ribonuclease resistant structures could be useful as RNA standards.

RNA bacteriophages have long been used as model systems to study the mechanisms of RNA replication and translation. The RNA genome within RNA bacteriophages is resistant to ribonuclease digestion due to the protein coat of the bacteriophage. Bacteriophage are simple to grow and purify, and the genomic RNA is easy to purify from the bacteriophages. These bacteriophages are classified into subgroups based on serotyping. Serologically, there are four subclasses of bacteriophage, while genetically, there are two major subclasses, A and B (Stockley, 1994; Witherell, 1991). Bacteriophage MS2/R17 (serological group I) have been studied extensively. Other well-studied RNA bacteriophages include GA (group II), Q-beta (group III), and SP (group IV). The RNA bacteriophages only infect the male strains of *Escherichia coli*, that is, those which harbor the F' plasmid and produce an F pilus for conjugation.

The MS2 bacteriophage is an icosahedral structure, 275 Å in diameter, and lacks a tail or any other obvious surface appendage (Stockley, 1994). The bacteriophage has large holes at both the 5- and 3-fold axes which might be the exit points of the RNA during bacterial infection. The MS2 bacteriophage consists of 180 units of the bacteriophage Coat Protein (~14 kDa) which encapsidate the bacteriophage genome (see reviews, Stockley, 1994; Witherell, 1991). The MS2 RNA genome is a single strand encoding the (+) sense of 3569 nucleotides. The genes are organized from the 5' end as follows: the Maturase or A protein, the bacteriophage Coat Protein, a 75 amino acid Lysis Protein, and a Replicase subunit. The Lysis gene overlaps the Coat Protein gene and the Replicase gene and is translated in the +1 reading frame of the Coat Protein. Each bacteriophage particle has a single copy of Maturase which is required for interacting with the F pilus and thus mediating bacterial infection.

Packaging of the RNA genome by Coat Protein is initiated by the binding of a dimer of Coat Protein to a specific stem-loop region (the Operator or "pac" site) of the RNA genome located 5' to the bacteriophage Replicase gene. This binding event appears to trigger the complete encapsidation process. The sequence of the Operator is not as critical as the stem-loop structure. The Operator consists of 21 nucleotides and only two of these residues must be absolutely conserved for Coat Protein binding.

The viral Maturase protein interacts with the bacteriophage, genomic RNA at a minimum of two sites in the genome (Shiba, 1981). It is evidently not required for packaging. However, its presence in the bacteriophage particle is required to preserve the integrity of the genomic RNA against ribonuclease digestion (Argetsinger, 1966; Heisenberg, 1966).

Attempts to produce a viable, infectious recombinant RNA (reRNA) bacteriophage have been unsuccessful. The bacteriophage are very efficient at deleting heterologous sequences and the fidelity of the Replicase is poor such that point mutations occur at the rate of $\sim 1 \times 10^{-4}$.

Pickett and Peabody (1993) performed studies in which a non-bacteriophage RNA was encapsidated by MS2 Coat Protein. Their apparent goal was to determine if the 21 nucleotide Operator (pac site) would confer MS2-specific packageability to non-bacteriophage RNA in vivo. *E. coli* was co-transformed with two plasmids: one encoding MS2 Coat Protein and the other encoding β-galactosidase (lacZ). The lacZ gene was modified such that it had the MS2 Operator sequence cloned upstream of it. The *E. coli* were induced such that the Operator-lacZ hybrid RNA was co-expressed with the MS2 Coat Protein. The Coat Protein dimer bound to the Operator, triggering the encapsidation of the lacZ RNA to form "virus-like particles". The virus-like particles were purified by a CsCl gradient. The buoyant density of these virus-like particles had a much greater density distribution than did the wild-type MS2 bacteriophage. The MS2 banded tightly at 1.45 g/cc whereas the virus-like particles ranged in density from 1.3 to 1.45 g/cc, suggesting substantial heterogeneity in the RNA content of the virus-like particles. In other words, the Pickett and Peabody virus-like particles were packaging different lengths of RNA and/or different species of RNAs.

The results of the Pickett and Peabody work were not as expected. The lacZ RNA purified from these virus-like particles was degraded to a major species of ~500 bases as opposed to the expected full length 3000 bases. This 500 base RNA was only detectable by the sensitive Northern blotting procedure. The authors did not know if the degradation occurred before or after encapsidation, but suggested that these viral-like particles may be sensitive to ribonuclease digestion. It was found that the majority of the RNA packaged was actually 2 species, 1800 bases and 200 bases in size. These two RNA fragments were easily detected after gel electrophoresis and methylene blue staining. The 500 base Operator-lacZ RNA fragment was not visible by methylene blue staining. It was only detected by Northern blotting using a lacZ probe. These authors concluded that the 0.2 and 1.8 kb RNAs were derived from *E. coli* pre-16S rRNA. The host *E. coli* RNA was packaged in preference to the Operator-lacZ RNA indicating that the specificity of the Pickett and Peabody bacteriophage packaging system was poor.

In other studies, Pickett and Peabody modified the packaging of the Operator-lacZ RNA by changing the ratios of the Coat Protein and Operator-lacZ RNA produced in *E. coli*. By increasing the concentration of the Operator-lacZ RNA and decreasing the concentration of the Coat Protein, they were able to encapsidate mainly the Operator-lacZ RNA and no detectable pre-16S rRNA. These results suggested that the original Pickett and Peabody packaging strategy suffered in specificity because they were unable to reach and maintain the appropriate molar ratio of Coat Protein to Operator-lacZ RNA optimal for packaging the target RNA. Even in the second set of packaging studies, the concentrations of the Coat Protein and Operator-lacZ RNA were only coarsely adjusted. The Pickett and Peabody system had no feedback mechanism to maintain the optimal ratio of Coat Protein to Operator-lacZ RNA for packaging.

In their second set of packaging studies, Pickett and Peabody did not characterize the RNA that was packaged with the modified procedure. The RNA was not purified from the virus-like particles and assessed by, for example, gel electrophoresis. Furthermore, the virus-like particles in this study or the previous study were not characterized for their ability to protect the encapsidated lacZ RNA from ribonucleases. There was no discussion as to the yield of virus-like particles or Operator-lacZ RNA obtained from the Pickett and Peabody studies.

Currently, there are two major methods for the synthesis of RNA species of a specific sequence: chemical synthesis and in vitro transcription. Although the chemical synthesis of RNA can produce very pure product, it is both expensive and it is limited to synthesizing oligonucleotides not much longer than 30 bases. Chemical synthesis is most suitable for generating antisense RNA oligonucleotides, which are generally 15 to 30 bases in length. However, most of the applications for RNA, such as probe synthesis and in vitro and in vivo translation, require longer RNA products, in the range of 100 bases to several kilobases.

RNA synthesis by in vitro transcription became a practical method as developed by Melton et al. (1984). The RNA polymerase from bacteriophage SP6 was used to transcribe DNA templates containing an SP6 bacteriophage promoter. Since then, promoter/polymerase systems have been developed for the T7 and T3 bacteriophages as well. These in vitro systems require a bacteriophage RNA polymerase, a DNA template encoding a phage promoter upstream of the sequence to be transcribed, an appropriate buffer and ribonucleotides. Each of these components must be ultrapure and free of ribonucleases to prevent degradation of the RNA product once it is transcribed. Conditions have been optimized which generate 100 to 150 µg of RNA from 1 µg of template (MEGAscript U.S. Pat. No. 5,256,555). Although in vitro transcription is currently the best method of synthesizing long RNA sequences, it is expensive for very large scale production in terms of gram quantities of product due to the-large quantities of ultrapure enzymes, nucleotides and buffers needed. Yet, such large quantities of RNA are needed for example in vaccination or gene therapy where transient gene expression is desired.

RNA bacteriophage capsids have been assembled in vitro to act as a drug delivery system, called Synthetic Virions (Stockley, 1994). The Operator RNA is synthesized chemically and then conjugated to therapeutic oligonucleotides (antisense DNA/RNA or ribozymes) or cytotoxic agents (ricin A chain). The conjugated Operator is then mixed with Coat Protein in vitro to trigger specific encapsidation of the non-phage molecules. The Synthetic Virions are conjugated to ligands which promote uptake in cells by receptor mediated endocytosis. Once inside the cell, the Synthetic Virions disassemble and release the therapeutic molecule. The disassembly of the Synthetic Virion is facilitated by the low pH of the endosomal compartments.

RNA has been used to transfect cells in vitro and in vivo to produce transient expression of the encoded protein. One of the applications for RNA transfection is cancer vaccination (Conry, 1995). RNA has the advantage that expression is transient due to its lability and it is not able to integrate into the host's genome. The use of DNA for nucleic acid vaccination with oncogenes could possibly induce neoplasms. The DNA could integrate into the host genome, leading to a malignant transformation. DNA encoding an oncogene may replicate within cells over periods of months leading to the expression of the oncogene product over the same time period. It has been demonstrated that prolonged expression of some oncogenes in cells may result in their transformation. The current methods for delivering RNA into cells is either injecting naked RNA, cells from tissue culture mixed with naked RNA, or RNA complexed with cationic liposomes into the tissue of an animal (Lu, 1994; Dwarki, 1993). A problem with these delivery systems is the susceptibility of the RNA to ribonucleases in the tissue culture medium or in the extracellular fluids of the host. Transfection efficiency diminishes if the mRNA is degraded before it can reach its target. Transfection efficiency would be improved by increasing the half-life of the RNA prior to its entry into the cell.

SUMMARY OF THE INVENTION

The present invention contemplates various aspects and uses of nuclease resistant nucleic acids. The invention contemplates various methods of making such nuclease resistant nucleic acids. The invention contemplates the use of viral-like systems to produce large amounts of nucleic acid. In preferred embodiments, this nucleic acid is ribonuclease resistant. The invention contemplates the use of nuclease resistant nucleic acids, particularly ribonuclease resistant nucleic acids, in various diagnostic assays.

A primary aspect of the invention is the preparation and use of nuclease resistant nucleic acid standards. Internal standards play an important role in confirming test results. They also provide a means for quantification. The detection and quantification of specific RNAs in samples has become prevalent with the advent of RT-PCR™. The internal standard for RT-PCR™studies should be an RNA molecule, as it controls for both the reverse transcription and PCR™ amplification steps. This is problematic, as RNA is particularly susceptible to RNase degradation. Altered test results could be produced by partial or complete degradation of an RNA standard either during storage or after introduction to a sample. The likelihood of at least partial RNA degradation is quite high, given that many of the RNA detection schemes are designed to detect viral RNAs in is serum samples, where relatively high quantities of various RNases are located. The ideal internal standard for RNA diagnostic assays is a molecule that is functionally equivalent to RNA in the assay format, but resistant to degradation by nucleases. Three general methods can be imagined for protecting RNA from enzyme-mediated degradation in an environment in which RNases are active: (1) microencapsulating the RNA inside an impenetrable structure, (2) non-covalently binding the RNA with molecules that deny access of nucleases to the standard, and (3) chemically altering the structure of the RNA in such a way that it is no longer a substrate for nucleases while still being functionally equivalent to RNA in the assay format. A more detailed description, examples, and enablements for each are provided below.

The nucleic acids in the standards of the invention can be used in quantifying assays. These standards may be used for a variety of purposes such as quantitative RNA standards (to determine the absolute copy number of a specific RNA sequence), specifically to quantify the number of RNA viruses such as HIV-1, HIV-2, HCV, HTLV-1, HTLV-2, hepatitis G, enterovirus, dengue fever virus, or rabies, in plasma, serum, or spinal fluid. They may also be used to quantify the expression of specific mRNA in cells or tissue by an RT-PCR™ assay. The standards may be internal or external. An internal standard is mixed with the sample at a known concentration such that the sample and the standard are processed and assayed as one. Thus, differences in the efficiency of the assay from sample to sample are normalized using the signal generated by the internal standard. An external standard is processed and assayed at a known concentration in parallel with the sample but it is processed separately from the sample. Several different concentrations of the external standard may be processed simultaneously to produce a standard curve which may then be used to determine the value of the unknown sample. Internal and external standards may both be used for quantification but internal standards are generally regarded as more accurate. The standards may be used as qualitative standards acting as positive controls in diagnostics, for example, bacterial, fungal, or parasitic diseases which are diagnostics RNA based or in RT-PCR™ assays to indicate that all of the reagents are functioning properly. These standards may be used to measure the integrity of an RNA isolation procedure by measuring the amount of degradation observed in the protected RNA after it has been subjected to the isolation procedure followed by Northern blotting. They may be used as environmental tracers to follow the flow of groundwater or to label the waste of individual companies with a unique nucleic acid sequence which can be traced back to the offending company.

The present invention is particularly useful for viral quantification. There are many new nucleic acid based assays in the process of being developed and/or marketed, i.e., Roche Diagnostic Systems, Amplicor™ HIV Monitor™ and Amplicor™ HCV Monitor tests; Organon Teknika, NASBA HIV kit; GenProbe, Transcription Mediated Amplification HIV kit; and Chiron Corp., branched DNA (bDNA) signal amplification assay for HIV and HCV. These assays detect pathogenic human viruses such as HIV and HCV in human plasma or serum. These assays are highly sensitive, detecting even less than 300 virions per 1.0 ml of plasma. In their current format, several of these nucleic acid based assays use naked RNA for their quantitative standards. Unfortunately, these naked RNA standards are very susceptible to ribonuclease degradation and thus the results of the assay may be compromised.

One primary embodiment of the present invention relates to nucleic acid standards comprising nuclease resistant recombinant nucleic acid segments comprising a sequence coding a standard nucleic acid. In some preferred embodiments, the nucleic acid standard is an RNA standard comprising a ribonuclease resistant RNA segment comprising a sequence coding a standard RNA. As used herein the terms "standard nucleic acid" and "standard RNA" refer respectively to nucleic acids and RNAs that are suitable for use as a standard in the particular assay to be employed. The present invention contemplates a ribonuclease resistant recombinant RNA which is highly suitable as an RNA standard for quantifying RNA viruses, although it need not be recombinant and may be used as an RNA standard for RNA isolated from any source, such as cells from tissue cultures. In particular, the structure of an RNA bacteriophage may be modified to package a recombinant RNA (reRNA) molecule. The reRNA sequence serves as an RNA standard for the quantification of a particular RNA sequence/target.

In regard to the invention, the terms "nuclease resistant" and "ribonuclease resistant" mean that a nucleic acid exhibits some degree of increased resistance to nuclease over a naked, unmodified nucleic acid of the same sequence.

There are a variety of methods that may be employed to render a nucleic acid segment nuclease resistant The nucleic acid segment may be chemically modified, coated with a nuclease resistant coating, or caged in a nuclease resistant structure. For example, the RNA standard can be a chemically modified RNA that is resistant to ribonuclease. Another way in which to render a recombinant RNA segment ribonuclease resistant is to coat it with a ribonuclease resistant coating. Such a coating can be anything that binds in a sequence dependent or independent manner to the RNA and renders the RNA ribonuclease resistant. In some cases, the RNA standard is a recombinant RNA that is caged in a ribonuclease resistant structure. Methods of caging RNA involve the partial encapsidation of the RNA in viral proteins, partial lipid encapsulation of the RNA, partially trapping the RNA in polymer matrices, etc.

In some preferred embodiments of the invention, the ribonuclease resistant structure is comprised of a viral Coat protein that partially encapsidates the RNA standard. The RNA is transcribed in vivo in a bacterial host and then encapsidated by bacteriophage proteins. This "caging" of the RNA results in RNA which is protected from ribonuclease (Armored RNA™). Although the nucleic acid or RNA may be completely or substantially caged in the nuclease resistant structure, partially caged nucleic acids and RNAs are also within the scope of the present invention as long as the partial caging renders the nucleic acid or RNA nuclease or ribonuclease resistant. Thus, when used herein the terms "encapsidation," "encapsulation," "trapped," etc. encompass structures wherein the encapsidation, encapsulation, trapping etc. is partial as well as substantial or substantially complete so long as the resultant structure is nuclease or ribonuclease resistant as those terms are used herein.

In a specific preferred embodiment, the invention relates to a ribonuclease resistant recombinant RNA ("reRNA") standard. These Armored RNA™ (AR) standards are ribonuclease resistant due to the encapsidation of the reRNA by bacteriophage proteins. The intact RNA is easily extracted from the Armored RNA™ standard particles by common RNA extraction methods such as the guanidinium and phenol method (Chomczynski, 1987). The non-bacteriophage RNA may be used in many applications: as an RNA standard for quantification, as RNA size standards, and for transient gene expression in vitro and in vivo.

The Armored RNA™ can be calibrated to serve as RNA standards in quantitative assays to determine the absolute number of RNA viruses within a plasma sample. The Armored RNA™ can be subjected to extreme ribonuclease treatment without any degradation of the RNA standard. Armored RNA™ is very durable and can be stored for an indefinite time at 4° C., or even room temperature, in the presence of ribonucleases. There is no known RNA standard with these qualities. Armored RNA™ differs in several features from prior art virus-like particles such as those of Pickett and Peabody. The bacteriophage sequence of the reRNA of the Pickett and Peabody particles consisted only of the Operator sequence (or pac site) which is required for Coat Protein recognition of the RNA to initiate packaging. The Armored RNA™ contains about 1.7 kb of bacteriophage RNA sequence encoding the Maturase, the Coat Protein and the pac site. The inclusion of the long stretch of bacteriophage sequence within the packaged reRNA may contribute substantially to forming a macromolecular structure most similar to the wild-type MS2 structure. Further, there may be other, as of yet uncharacterized, sequences within the bacteriophage RNA that recognizes Coat Protein and Maturase that contribute to assembling the bacteriophage particle into a structure that protects the packaged RNA. Non-bacteriophage RNAs can be packaged by Coat Protein alone as demonstrated by Pickett and Peabody but these non-bacteriophage RNA sequences are not entirely ribonuclease resistant. Besides maximizing the possibility of assuming the correct bacteriophage structure, the inclusion of the extra bacteriophage sequence in the Armored RNA™, as opposed to the Pickett and Peabody virus like particles, also increases the specificity of the RNA to be packaged by the bacteriophage proteins. The Pickett and Peabody virus like particles contained mainly the host *E. coli* pre-rRNA over the target RNA unless the ratio of the Coat Protein to reRNA was decreased.

A preferred strategy for synthesizing the Armored RNA™ is one that has been optimized by producing a self-regulating feedback mechanism to maintain the optimal ratio of Coat Protein to reRNA for assembly. The Coat Protein is encoded in the reRNA and the reRNA is only available for translation in its unassembled form. Thus, when the appropriate concentration of Coat Protein has been translated from the reRNA, it begins to package the reRNA. More Coat Protein cannot be translated until more reRNA is transcribed from the recombinant plasmid. The Pickett and Peabody strategy lacked a mechanism for maintaining a constant ratio between these two molecules. Pickett and Peabody used a trans mechanism for packaging the Operator-lacZ RNA. The Coat. Protein RNA was transcribed from a different plasmid and therefore, the Coat Protein was being translated from a different RNA than it was to package. Since there is no Operator on the Coat Protein RNA, the Coat Protein RNA is continually being transcribed and the Coat Protein is continually being translated. After induction, there is no regulation of the synthesis of the Coat Protein. Similarly, there is no control of the transcription of the Operator-lacZ RNA. Thus the transcription of both RNAs is constitutive and translation of the Coat Protein is constitutive. In contrast, in some embodiments, the Armored RNA™ method is a cis method where the Coat Protein is being translated from the same RNA that is to be packaged. The production of the Coat Protein is regulated at the level of translation because once the concentration of Coat Protein is high enough, it encapsidates the RNA from which it is being translated and thus prevents any further Coat Protein from being translated from that RNA. By this autoregulatory method, the levels of Coat Protein cannot become so high that RNA is encapsidated in a non-specific fashion.

Armored RNA™ may be produced using minimal bacteriophage sequence that encodes the binding sites for Maturase and Coat Protein (or even less) while providing the Maturase and Coat Protein in trans. The maximal size of RNA that can be encapsidated and remain ribonuclease resistant remains to be defined. However, the wild type MS2 bacteriophage contains an RNA genome of ~3.6 kb. Since the structure of these bacteriophage is iscosahedral, it is likely that the maximal size will be ~4 kb. Thus, the potential to replace the sequences encoding the Maturase and the Coat Protein with a foreign sequence relevant to the user, may be advantageous. One skilled in the art can readily perform a systematic set of studies to determine the minimal amount of bacteriophage sequence necessary to produce Armored RNA™. One advantage of Armored RNA™ in these applications is that they are non-replicative and therefore, aberrantly high signals would not be detected due to viral replication.

The stability of Armored RNA™ indicates that the packaged RNA may withstand extreme environmental conditions. This property may be useful in using Armored RNA™ as molecular markers to trace the origin of pollutants. For instance, the Armored RNA™ could be spiked into the waste containers of different companies. The Armored RNA™ for each company would contain a unique nucleotide sequence which would identify that company. In the event of a spill, a sample would be taken, RNA would be isolated and RT-PCR™ performed to determine the unique sequence of the Armored RNA™ and identify the company responsible for the spill. In a related application, the Armored RNA™ could be used by environmentalists to trace the flow of groundwaters.

There are many possible methods of creating genes that, when expressed in vivo, will result in Armored RNA™ compositions in which RNA is protected against ribonuclease in a viral Coat Protein synthesized in vivo.

In order to understand some aspects of the invention, it is necessary to understand the components of a bacteriophage, for example, the MS2 bacteriophage. The RNA genome is ~3.6 kb and encodes 4 different proteins: the Maturase, the Coat Protein, the Lysis Protein and the Replicase. The Coat Protein composes most of the mass of the MS2 bacteriophage particle. It is a small protein of ~14 kD in size but there are 180 molecules of this protein which encapsidate each molecule of the bacteriophage RNA genome. In total, the Coat Protein molecules provide ~2,500 kD of the total bacteriophage mass of ~3,500 kD. There is one molecule of Maturase protein per bacteriophage particle which is ~44 kD in size. The Maturase serves to protect the RNA genome from ribonuclease degradation and it is the receptor for the F pilus for *E. coli* infection. The Lysis Protein and the Replicase are not a component of the bacteriophage molecule. The Lysis Protein is involved in lysing the *E. coli* cell to release the bacteriophage particles. The Replicase protein and 3 other *E. coli* host proteins compose a protein complex which is responsible for replicating the RNA genome and synthesizing a large number of copies for packaging.

In this application, cis refers to a protein binding to the same RNA transcript species from which it was translated. Trans refers to a protein binding to an RNA transcript species other than the RNA transcript species from which it was translated.

The simplest composition may be Coat Protein and a RNA encoding a non-bacteriophage sequence either with or without encoding one or more Operator sequences. Another composition may comprise Coat Protein and a reRNA encoding one or more Operators and a non-bacteriophage sequence.

Another composition may be Coat Protein and Maturase and a reRNA encoding one or more Operator sequences, one or both Maturase Binding sites and non-phage sequence. The Coat Protein and the Maturase are provided in trans.

Another composition may be Coat Protein and a reRNA encoding Coat Protein, one or more Operator sequences and non-phage sequence. Including more than one Operator may serve to endow extra protection against ribonucleases and increase the specificity of the Coat Protein for the reRNA over host RNA.

Another composition may be Coat Protein and Maturase and a reRNA encoding Coat Protein, Operator sequence, Maturase Binding site and non-phage sequence. The Maturase protein is provided in trans.

Another composition may be Coat Protein and Maturase and a reRNA encoding Coat Protein, Maturase (which includes a Maturase binding sites), one or more Operator sequences and non-phage sequence.

Another composition may be Coat Protein and Maturase and a reRNA encoding to Coat Protein, Maturase (which includes a Maturase binding sites), one or more Operator sequences, the Maturase Binding Site located at the 3' end of the MS2 genome and non-phage sequence.

Another composition may be Coat Protein and Maturase and a reRNA encoding Coat Protein, Maturase, one or more Operator sequences, most of the C-terminal coding region of the Replicase (so that none of the protein is synthesized in vivo). Further, this composition may comprise a sequence coding the entire active Replicase such that the Replicase will function.

Another composition may be Coat Protein and Maturase and a reRNA encoding Coat Protein, Maturase, one or more Operator sequences, most of the C-terminal coding region of the Replicase (so that none of the protein is synthesized in vivo) and the Maturase Binding Site located at the 3' end of the MS2 genome and non-phage sequence.

In some embodiments, there will be no need to have an Operator sequence to package RNA. The co-expression of Coat Protein and RNA can lead to operator-less RNA being packaged and protected in a manner that may be less specific than produced when an Operator sequence is present.

Other compositions may comprise any of the above, in conjunction with the Lysis Protein. The Lysis Protein may be provided in either.

In each of these compositions, the non-phage RNA may be positioned at a variety different regions of the reRNA. For example, in the first composition, the reRNA may encode 2 Operators and non-phage RNA Both Operators may be located 5' or 3' of the non-phage RNA or there may be one Operator at each end of the non-phage RNA. If there is only a single Operator, it may be preferable to position it at the 3' end of the full-length transcript so that only full-length transcripts are packaged. Including a Maturase Binding Site near the 3' end may have a similar advantage towards packaging full length RNA. In the wild-type phage genome, the Maturase Binding Sites are located within the Maturase coding sequence and at the 3' end of the genome. In the compositions where the Coat Protein is provided in trans, it is preferable that there is no Operator sequence encoded on the same RNA transcript as the Coat Protein or the Coat Protein may bind to both the Coat Protein RNA transcript and the non-phage-Operator RNA, producing a mixed population of capsids.

Using more than one Operator sequence per RNA molecule may be expected to increase the specificity of the Coat Protein for the target RNA and decrease the possibility of packaging host RNA in vivo as in the Pickett and Peabody studies. In vitro studies investigating the binding kinetics of Coat Protein with the Operator sequence demonstrated that Coat Protein bound in a cooperative manner to an RNA molecule encoding two Operator sequences and that the Coat Protein bound to the RNA with two Operators at a much lower concentration than an RNA with a single Operator (Witherell, 1990). Increasing the specificity of binding may also be accomplished using a mutant Operator sequence with a higher affinity for Coat Protein than the wild type sequence (Witherell, 1990).

Major aspects of the invention may be summarized as follows. One primary embodiment of the present invention relates to nucleic acid standards comprising nuclease resistant nucleic acid segments comprising sequences coding a standard nucleic acid. In some preferred embodiments, the nucleic acid standard is an RNA standard comprising a ribonuclease resistant RNA segment comprising a sequence coding a standard RNA.

There are a variety of forms ribonuclease resistant RNA standards that can be employed. The RNA can be chemically modified RNA that is resistant to ribonuclease. A chemically modified RNA may be comprised of chemically modified nucleotides. These nucleotides are modified so that ribonucleases cannot act on the RNA. The chemically modified RNA is prepared by chemical modification of an RNA or a previously transcribed RNA transcript. Alternatively, the chemically modified RNA may be transcribed or synthesized from nucleotides that have already been chemically modified.

An RNA standard may also comprise an RNA that is bound non-covalently, or coated with, a ribonuclease resistant coating. Such binding, which may be sequence dependent or independent, renders the RNA ribonuclease resistant. In some embodiments, the bound molecule is comprised of a protein. Examples of such binding proteins are MS2/R17 coat protein, HIV-1 nucleocapsid protein, gp32, the regA protein of T4, or the gp32 of bacteriophage T4. In other cases, the non-covalently bound molecule is comprised of a small molecule. For example the polyamines, spermine and/or spermidine. The ribonuclease-resistant coating may also be comprised of a nucleic acid. In some preferred embodiments, the nucleic acid hybridizes to the recombinant RNA, blocks nucleases, and can serve as a primer for reverse transcriptase. In other cases, poly-L-lysine and cationic detergents such as CTAB may be used to coat and protect RNA.

In other embodiments of the invention, the ribonuclease resistant RNA segment is a caged ribonuclease resistant structure, that is, the RNA segment is partially encapsulated in a ribonuclease resistant structure. For example, the ribonuclease resistant structure may be comprised of lipids. In some cases, a lipid ribonuclease resistant structure will comprise a liposome. In other embodiments, the ribonuclease resistant structure is a synthetic microcapsule, such as a polymer matrix. Some examples of useful polymer matrices comprise agarose or acrylamide.

In some preferred embodiments, the invention contemplates a nucleic acid standard comprising a ribonuclease resistant structure comprising a standard nucleic acid segment encapsidated in viral Coat Protein. A preferred embodiment of the invention contemplates an RNA standard comprising a ribonuclease resistant RNA segment comprising a sequence coding a standard RNA Encapsidation of a RNA segment in a viral Coat Protein can render it resistant to ribonuclease, hence the term Armored RNA™.

The viral Coat Protein may be any native or modified viral Coat Protein, but, in many preferred embodiments, the viral Coat Protein is a bacteriophage viral Coat Protein. Such bacteriophage viral Coat Proteins may be of an *E. coli* bacteriophage of genetic subclass A or B; in some preferred embodiments, the bacteriophage viral Coat Protein is of an *E. coli* bacteriophage of genetic subclass A. A bacteriophage viral Coat Protein can be of an *E. coli* bacteriophage in serological group I, II, II, or IV, with some preferred embodiments employing a bacteriophage viral Coat Protein from *E. coli* bacteriophage of to serological group I. In certain specifically preferred embodiments, the bacteriophage viral Coat Protein is of an MS2/R 17 bacteriophage. The bacteriophage viral Coat Protein may also be of a *Pseudomonas aeruginosa* RNA bacteriophage, for example, the *Pseudomonas aeruginosa* PRR1 or PP7 bacteriophage. The bacteriophage viral Coat Protein may further be of a filamentous bacteriophage, and, because such bacteriophage can comprise a longer RNA segment than many other bacteriophage, this is an embodiment of particular interest. It is also contemplated that the bacteriophage of the archae bacteria will be useful in the invention (Ackerman, 1992). Of course, the viral Coat Protein need not be from a bacteriophage, and the invention contemplates viral Coat Proteins from plant or animal virus, for example, tobacco mosaic virus (Hwang 1994a; Hwang, 1994b; Wilson, 1995), the alphaviruses (Frolov, 1996), HBV, feline immunodeficiency virus, and Rous sarcoma virus will all be useful. The viral Coat Protein may be a native or a modified viral Coat Protein. Modified viral Coat Proteins may be used to obtain certain desirable characteristics, such as greater or lesser viral coat resistance. Modified viral Coat Proteins may be made by any of a number of methods known to those of skill in the art, including PCR™-based and other forms of site-directed mutagenesis.

In certain preferred embodiments, the ribonuclease resistant RNA segment is bound to a viral Maturase protein. For example, the RNA standard may comprise a viral Maturase protein bound to a viral Maturase binding site on a recombinant RNA segment The viral Maturase protein and/or viral Maturase protein binding site may be native or modified. Modifications in the base sequence of the Maturase binding site and in the amino acid sequence of the Maturase may be made by any of a number of methods known to those of skill. A viral Maturase binding site is found in the RNA sequence that encodes a native Maturase. Therefore, the RNA sequence may contain within itself an RNA coding for the Maturase. Further, since Maturase binding is purported to have some effect on the stability of RNA segments, it is contemplated that multiple Maturase binding sites and/or Maturase coding sequences may be included in the RNA segment.

The RNA segment which codes for a standard ribonucleic acid may also comprise a sequence coding a Replicase protein, and the Replicase protein may or may not be expressed or expressible from that sequence. In certain preferred embodiments, the sequence coding the Replicase protein codes a modified Replicase protein that is not active.

The RNA segment will typically comprise an Operator coding sequence, and, in many preferred embodiments, a viral Maturase protein binding site which may be included in a viral Maturase protein coding sequence. The RNA segment may further comprise a viral Coat Protein coding sequence of the type discussed above.

There are many embodiments of the RNA segment comprising a sequence coding a standard RNA, a few examples of which are given below. In some very basic embodiments, the RNA segment comprises an Operator sequence and a viral Coat Protein sequence. In other basic embodiments, the RNA segment comprises an Operator sequence, a viral Coat Protein sequence, and a non-bacteriophage sequence. In other embodiments, the RNA segment comprises at least two Operator sequences and a non-bacteriophage sequence.

The RNA segment may comprise an Operator sequence, a sequence coding a viral Maturase protein, and a non-bacteriophage sequence. Further, in some preferred embodiments, the RNA segment comprises an Operator sequence, a sequence coding a viral Maturase protein, a sequence coding a viral Coat Protein and a non-bacteriophage sequence. The RNA segment may comprise an Operator sequence, at least two viral Maturase binding sites, a sequence coding a viral Maturase protein, a sequence coding a viral Coat Protein and a non-bacteriophage sequence. Alternatively, the RNA segment may comprise an Operator sequence, at least two viral Maturase binding sites, a sequence coding a viral Maturase protein, a sequence coding a viral Coat Protein, a non-bacteriophage sequence, and a sequence coding a Replicase protein. The RNA may comprise all or part of the recombinant RNA segment coded for in the sequence of pAR-1 or pAR-2.

In some preferred embodiments, the RNA segment comprises a bacteriophage sequence from an RNA bacteriophage and a non-bacteriophage sequence. The non-bacteriophage sequence may be inserted into a multiple cloning site. The non-bacteriophage sequence may be a viral, bacterial, fungal, animal, plant, or other sequence, although, in certain preferred embodiments it is a viral sequence. Multiple Operators may be on either terminus of the non-bacteriophage sequence, or may flank the sequence. Multiple Operator sequences may be useful for packaging larger non-bacteriophage sequences.

The non-bacteriophage sequence is often a sequence adapted for use as a standard in detection and/or quantification of an RNA by, for example, PCR™-based procedures. In specific embodiments, the non-bacteriophage sequence is a sequence adapted for use in detection and/or quantification of an RNA of diagnostic value. For example, the non-bacteriophage sequence can be a sequence adapted for use as a standard in detection and/or quantification of HIV-1, HIV-2, HCV, HTLV-1, HTLV-2, hepatitis G, an enterovirus, or a blood-borne pathogen. In some particularly interesting embodiments, the non-bacteriophage sequence is adapted for use in the detection of such viral diseases as HIV-1, HIV-2, HCV, HTLV-1, or HTLV-2. Adaptation of the non-bacteriophage sequence can be accomplished in any manner that will render the sequence suitable for detection and/or quantification of the tested RNA. In some embodiments, the non-bacteriophage sequence adapted for use as a standard in detection and/or quantification of an RNA of interest by modifying the native RNA sequence to be detected or monitored so that it is distinguishable from the native sequence. For example, detection and/or quantification of HIV-1 can be accomplished with a non-bacteriophage sequence comprising a modified HIV-1 sequence. The RNA standard may comprise a non-bacteriophage sequence adapted for use as a standard in detection and/or quantification of a blood-borne pathogen, such as a plasmodium, trypanosome, *Francisella tularensis*, or *Wucheria bancrofti*.

The bacteriophage sequence of the RNA standard may be a sequence from any *E. coli* bacteriophage of any genetic subclass, for example, subclass A. Further the bacteriophage sequence may be a sequence from an *E. coli* bacteriophage in serological group 1, II, II, or IV. In certain embodiments, the bacteriophage sequence is a sequence from an MS2/R17 bacteriophage. Of course, the bacteriophage sequence can also be a sequence from a *Pseudomonas aeruginosa* RNA bacteriophage, such as the PRR1 or PP7 bacteriophage, or a filamentous bacteriophage.

Other embodiments of the invention contemplate a RNA segment comprising various of the sequences discussed above. The RNA standard segment may be encapsidated in viral Coat Protein, or free from viral Coat Protein. For example, a recombinant RNA may be free of viral Coat Protein during the RNA standard production process or during an assay after isolation of the recombinant RNA segment from the viral Coat Protein. The RNA may be of any of the various forms discussed above, and may comprise Operator site(s), Maturase binding site(s), Coat Protein coding sequence(s), Maturase coding sequence(s), non-bacteriophage sequence(s), restriction enzyme sequence(s), active or non-active Replicase coding sequence(s), active or non-active Lysis Protein coding sequence(s) and/or other sequences.

The invention also contemplates DNA vectors adapted for use in the synthesis of a RNA standard comprising recombinant RNA segment encapsidated in viral Coat Protein. Such vectors are transfected into cells, for example *E. coli*, and function to cause the cells to produce RNA encapsidated in viral coat protein. A basic vector may comprise a sequence coding an Operator sequence and a viral Coat Protein sequence. Alternatively, the vector may comprise a sequence coding two Operator sequences and a non-bacteriophage sequence. In some embodiments, the vector may comprise a sequence encoding an Operator sequence, a sequence coding a viral Maturase binding site, and a multiple cloning site. The multiple cloning site may be either downstream or upstream of a sequence encoding a viral Maturase binding site. The vector may further comprise a sequence coding a viral Maturase protein and/or a Maturase binding site. The sequence coding the viral Maturase binding site may be comprised within the sequence coding the viral Maturase protein. Certain preferred embodiments comprise a sequence coding a viral Coat Protein gene, an Operator sequence, and a multiple cloning site. A DNA sequence coding a non-bacteriophage sequence may be inserted into the multiple cloning site of such a DNA vector, and the non-bacteriophage sequence may be any of the sequences discussed above.

The invention contemplates collection tubes containing a nucleic acid standard comprising recombinant nucleic acid encapsidated in viral Coat Protein. Such collection tubes may be adapted for use in collection of a body fluid such as blood, urine, or cerebrospinal fluid. For example, the collection tube may be a vacuum tube for the drawing of blood. Such collection tubes can streamline a diagnostic procedure by providing a nucleic acid standard in a body fluid sample at the time of drawing of the fluid and eliminating the need to add the standard as a part of the assay procedure.

The present invention contemplates methods for assaying for the presence of a tested nucleic acid in a nucleic acid sample using the nucleic acid standards described above. The "nucleic acid sample" may also be described herein as a nucleic acid composition. A nucleic acid composition, as used herein, is taken to mean any composition, usually a liquid composition that contains one or more nucleic acid molecules or polymers. The composition may also comprise buffers, salts, solvents, or solutes and the like, that are derived from a sample along with the nucleic acid composition, or that have been added to the composition during or after isolation. Such compositions are typically precipitated from an aqueous solution and resuspended. The nucleic acid standards may be internal or external standards. Such methods generally comprise the steps of: (1) obtaining a sample; (2) obtaining a nucleic acid standard comprising a nuclease resistant nucleic acid segment comprising a sequence coding a standard nucleic acid; (3) assaying the sample for the presence of a tested nucleic acid sequence; and (4) employing the nucleic acid segment comprising a sequence coding a standard nucleic acid as a standard in the assay. The methods may further comprise the step of isolating a nucleic acid composition from the sample. It is contemplated that samples may include, but would not be limited to inorganic materials such as a soil sample, any organic material, samples from a plant or animal, and may be tissue samples, or samples of blood or blood components. This method may further comprise isolating the nuclease resistant nucleic acid segment comprising a sequence coding a standard nucleic acid from a molecule that renders the nuclease resistant nucleic acid segment comprising a sequence coding a standard nucleic acid nuclease resistant to obtain a nucleic acid segment comprising a sequence coding a standard nucleic acid.

Alternatively, this method may further comprise admixing the sample or nucleic acid composition and the nucleic acid standard comprising a nuclease resistant nucleic acid segment comprising a sequence coding a standard nucleic acid prior to assaying for the presence of the tested nucleic acid sequence. This alternative method may further comprise isolating the nuclease resistant nucleic acid segment comprising a sequence coding a standard nucleic acid from a molecule that renders the nucleic acid segment comprising a sequence coding a standard nucleic acid nuclease resistant to obtain a nucleic acid segment comprising a sequence coding a standard nucleic acid. Additionally, the sample and the nucleic acid standard may be admixed prior to isolation of a nucleic acid acid composition from the sample and isolation of the nucleic acid segment comprising a sequence coding a standard nucleic acid so that isolation of the nucleic acid composition from the sample and the nucleic acid segment comprising a sequence coding a standard nucleic acid is performed in the same isolation procedure. This streamlines the procedure and assures that any tested nucleic acid and the nucleic acid standard are processed in parallel in the same reaction. Such parallel processing eliminates many variables that could compromise the results of the assay.

The assay may be any that would employ a nucleic acid standard, although many preferred embodiments comprise PCR™ analysis. One of the advantages of the nucleic acid standards of the invention is that they allow for quantitative assays, such as quantitative RT-PCR™. In RT-PCR™ procedures, the nucleic acid segment is typically an RNA comprising a sequence coding a standard RNA. Typically quantitative assays will comprise comparing an amount of tested RNA PCR™ product with an amount of standard RNA PCR™ product. RT-PCR™ analysis will usually comprise: (1) employing a reverse transcription procedure; (2) amplifying a nucleic acid sequence and generating a PCR™ product; and (3) detecting PCR™ product. In certain embodiments, the amplification step involves co-amplification of any tested RNA PCR™ product with standard RNA PCR™ product. Such co-amplification can be achieved via the use of a single primer set adapted for amplification of both tested RNA PCR™ product and standard RNA PCR™ product from an RT-PCR™ procedure.

The nucleic acid standards may be of any composition described either explicitly or implicitly above. For example, where ribonucleic acid standards are employed any form of ribonuclease resistant RNA segment comprising a sequence coding a standard RNA may be employed, including, but not limited to those involving chemical modification, ribonuclease resistant coating, or ribonuclease resistant caging.

The sequence coding the RNA standard may comprise a non-bacteriophage sequence, such as a viral sequence. The non-bacteriophage sequence may generally be a sequence adapted for use as a standard in detection and/or quantification of an RNA. In some preferred embodiments, the assay may be employed to detect and/or quantify viral loads in infection with HIV-1, HIV-2, HCV, HTLV-1, HThV-2, hepatitis G, an enterovirus, or a blood-borne pathogen. Presently more preferred embodiments contemplate the detection and/or quantification of HIV-1, HIV-2, or HCV using an RNA standard comprising a recombinant RNA with a modified HIV-1, HIV-2, or HCV sequence.

One specific method of the invention contemplates assaying for the presence of an RNA of diagnostic value by a method comprising: (1) obtaining a sample to be assayed; (2) obtaining an RNA standard comprising a sequence coding a standard RNA encapsidated in a bacteriophage Coat Protein; (3) admixing the sample with the RNA standard; (4) isolating RNA from the admixture; and (4) assaying for the presence of the RNA of diagnostic value with a RT-PCR™ analysis.

The invention contemplates methods of making a nucleic acid standard comprising a recombinant nucleic acid segment encapsidated in viral Coat Protein comprising: (1) obtaining a vector comprising a nucleic acid sequence coding a recombinant nucleic acid segment comprising a sequence coding an Operator sequence, and a non-bacteriophage sequence; (2) transfecting the vector into a cell; (3) providing a viral Coat Protein; and (4) culturing the cell under conditions allowing for transcription of the recombinant nucleic acid segment and encapsidation of the recombinant nucleic acid segment in viral Coat Protein. The recombinant nucleic acid segment may be RNA or DNA. The nucleic acid standard may be purified from the cells in which it is expressed by any of a number of manners known to those of skill for the separation of viral particles from cells. The cell may be any form of cell, although typically a bacterial cell, such as E. coli is employed.

Particularly preferred are methods of making RNA standards comprising a recombinant RNA segment encapsidated in viral Coat Protein, which methods comprise: (1) obtaining a vector comprising a DNA sequence coding a recombinant RNA segment comprising a sequence coding an Operator sequence and a non-bacteriophage sequence; (2) transfecting the vector into a cell; (3) providing a viral Coat Protein; and (4) culturing the cell under conditions allowing for transcription of the recombinant RNA segment and encapsidation of the recombinant RNA segment in viral Coat Protein. In many preferred embodiments, the recombinant RNA will comprise a Maturase binding sequence.

The provision of the viral Coat Protein can be by any number of means. For example, the protein can be expressed separately from the transcription of the recombinant RNA segment and added into the culture medium in a concentration such that the recombinant RNA becomes encapsidated once transcribed. However, in most preferred embodiments, the provision of the Coat Protein comprises: (1) obtaining a nucleic acid segment coding a viral Coat Protein; (2) transfecting the nucleic acid segment coding the viral Coat Protein into the cell; and (3) culturing the cell under conditions allowing for expression of the viral Coat Protein. In this embodiment, the nucleic acid segment coding the viral Coat Protein may be a DNA sequence comprised in the vector comprising the DNA sequence coding the recombinant RNA segment. The DNA sequence coding the viral Coat Protein may be located cis to the DNA sequence coding the recombinant RNA segment. Further, the DNA sequence coding the viral Coat Protein can be located in the DNA sequence coding the recombinant RNA segment. Alternatively, the DNA sequence coding the viral Coat Protein may be located trans to the DNA sequence coding the recombinant RNA segment, although this is not typical of preferred embodiments.

The method of making an RNA standard may comprise the further step of providing a viral Maturase protein. The provision of the viral Maturase protein can be by any number of means. For example, the protein can be expressed separately from the transcription of the recombinant RNA segment and added into the culture medium in a concentration such that the recombinant RNA becomes encapsidated once transcribed. However, in most preferred embodiments, the provision of the Maturase protein comprises: (1) obtaining a nucleic acid segment coding a viral Maturase protein; (2) transfecting the nucleic acid segment coding the viral Maturase protein into the cell; and (3) culturing the cell under conditions allowing for expression of the viral Maturase protein. In this case, the nucleic acid segment coding the viral Maturase protein may be a DNA sequence comprised in the vector comprising the DNA sequence coding the recombinant RNA segment. The DNA sequence coding the viral Maturase protein may be located cis to the DNA sequence coding the recombinant RNA segment. Further, the DNA sequence coding the viral Maturase protein can be located in the DNA sequence coding the recombinant RNA segment. Alternatively, the DNA sequence coding the viral Maturase protein may be located trans to the DNA sequence coding the recombinant RNA segment, although this is not typical of preferred embodiments. The recombinant RNA sequence, may, of course, be any of those discussed or suggested explicitly or implicitly above.

A preferred embodiment of the method of making an RNA standard comprising a recombinant RNA segment encapsidated in viral Coat Protein comprises: (1) obtaining a vector comprising a DNA sequence coding a recombinant RNA segment comprising a sequence coding an Operator sequence, a sequence coding a viral Maturase binding site, and a non-bacteriophage sequence; (2) transfecting the vector into a cell; (3) obtaining a DNA segment coding a viral Coat Protein and transfecting the nucleic acid segment coding the viral Coat Protein into the cell; (4) obtaining a DNA segment coding a viral Maturase protein and transfecting the nucleic acid segment coding the viral Maturase protein into the cell; and (5) culturing the cell under conditions allowing for transcription of the recombinant RNA segment, expression of the viral Coat Protein and the viral Maturase protein, and encapsidation of the recombinant RNA segment in viral Coat Protein. In preferred embodiments of this aspect of the invention, the DNA segment coding the viral Coat Protein is comprised in the vector comprising the DNA sequence coding the recombinant RNA segment. More preferably, the DNA sequence coding the viral Coat Protein is located cis to the DNA sequence coding the recombinant RNA segment. In preferred embodiments of this invention, the DNA segment coding the viral Maturase protein is comprised in the vector comprising the DNA sequence coding the recombinant RNA segment and, more preferably, located cis to the DNA sequence coding the recombinant RNA segment.

The invention also contemplates methods of making RNA in vivo comprising: (1) obtaining a vector comprising a DNA sequence coding a recombinant RNA segment comprising a sequence coding an Operator sequence, a sequence coding a viral Maturase binding site, and a non-bacteriophage sequence; (2) transfecting the vector into a cell; (3) obtaining a DNA segment coding a viral Coat Protein and transfecting the nucleic acid segment coding the viral Coat Protein into the cell; (4) obtaining a DNA segment coding a viral Maturase protein and transfecting the nucleic acid segment coding the viral Maturase protein into the cell; and (S) culturing the cell under conditions allowing for transcription of the recombinant RNA segment, expression of the viral Coat Protein and the viral Maturase protein, and encapsidation of the recombinant RNA segment in viral Coat Protein. These methods may further comprise the step of isolating the recombinant RNA segment from the Coat Protein, and this allows for the production of a large amount of desired RNA in vivo, ie., within bacterial cells. The isolated RNA segment may then be treated to obtain an RNA segment comprising the non-bacteriophage sequence. For example ribozyme sequences, RNase H and a complementary DNA oligonucleotide that function to generate sequence specific cuts in the RNA, or other molecular biology tools may be used to excise undesired RNA from the non-bacteriophage sequence, or a portion thereof The desired RNA segment may then be purified by means known in the art. The DNA vectors, RNA segments, cells, etc. employed and obtained in this method of in vivo transcription may be any of those described above.

The invention also contemplates methods of encapsidating a RNA segment in viral Coat Protein in vitro comprising: (1) obtaining a RNA segment comprising a sequence coding a standard RNA; (2) obtaining viral Coat Protein; and (3) placing the RNA segment comprising a sequence coding a standard RNA and the viral Coat Protein together under conditions causing the RNA segment comprising a sequence coding a standard RNA to become encapsidated in the viral Coat Protein.

The invention further contemplates methods of delivering RNA to cells in vitro or in vivo comprising: (1) obtaining an Armored RNA™ comprising a RNA segment comprising a sequence coding a standard RNA encapsidated in viral coat protein; (2) placing the Armored RNA™ culture with a cell; and (3) culturing the cell under conditions that cause the Armored RNA™ to be taken into the cell.

In such a method, the Armored RNA™ may comprise a bacteriophage protein that has been modified to facilitate delivery of RNA to a cell. For instance, the modified bacteriophage protein is a viral Coat Protein or a Maturase protein.

There are many different single and double stranded DNA bacteriophages which infect *E. coli* and other bacteria. Examples of single stranded DNA bacteriophage include φX174 and M13. Examples of double stranded DNA bacteriophage include T4, T7, lambda (λ), and phage P2. M13 and λ have been used extensively by molecular biologists and it is rather simple to create recombinants of these bacteriophage. As with the RNA bacteriophage, recombinants of the DNA bacteriophage could be constructed and quantified with specific DNA sequences to act as quantitative standards for particular DNA viruses using nucleic acid based assays. Some of the human DNA viruses are HSV, EBV, CMV, HBV, Parvoviruses, and HHV6. The benefit of these standards is that the DNA standards would be protected against DNases.

RNA synthesized by in vitro transcription may be packaged with bacteriophage proteins in vitro. This method would be useful towards protecting RNA species of very specific sequences, that is, the reRNA would not need to encode the Coat Protein and Maturase sequences. Only the binding sequences for Coat Protein and/or Maturase would be included within the RNA transcript and Coat Protein and/or Maturase would be provided exogenously. Encapsidation may occur co- or post-transcriptionally. It has been demonstrated that by combining RNA and Coat Protein under the appropriate conditions, the RNA will be encapsidated with Coat Protein to form a phage like particle (LeCuyer, 1995). Capsid formation by Coat Protein is stimulated by Operator sequence or long RNA transcripts (Beckett, 1988). Capsids will form without Operator sequence or any RNA but then the concentration of the Coat Protein must be much higher. to Therefore, the Coat Protein may be stored at a concentration which does not lead to capsid formation unless it is added to RNA. Using this strategy, the RNA may or may not require the Operator sequence, depending on the length and concentration of the RNA. This strategy may lend itself to packaging mRNA (RNA having a 5' cap and 3' polyA tail) which may then be used in transfection studies (see below). The Maturase may be required to form structures in which the packaged RNA is protected against ribonucleases.

RNA of different discrete lengths may be produced as Armored RNA™ in large quantities. The sizes could be mixed in equal mass amounts in their Armored RNA™ form. This mix may be heated in a denaturing solution and run on a denaturing formaldehyde agarose gel directly or the RNA may be purified from the mix and then run on a denaturing formaldehyde agarose gel as RNA size standards. Alternatively, chemically modified RNAs of different lengths may be transcribed which are ribonuclease resistant. These RNAs may be used as size standards in gel electrophoresis.

DESCRIPTION OF ILLUSTRATIVE EMBODIMENTS

Figure 1:
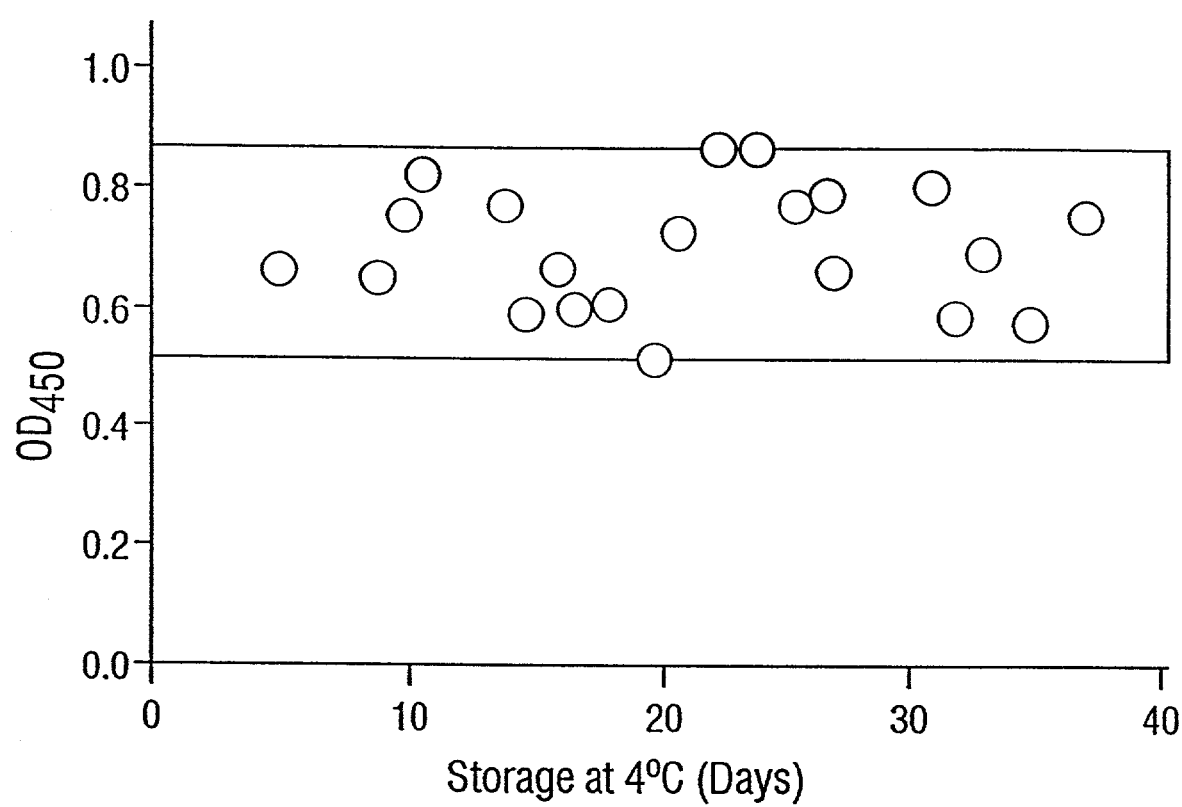
FIG. 1. Consistency of the signal produced by the AR-2 standard which was stored at 4° C. AR-2 standard (80 QS RNA equivalents) was added to 0.2 ml of HIV positive serum and processed using the Amplicor™ HIV Monitor™ test. Twenty one assays were performed over a 38 day period using the same stock of AR-2 standard stored at 4° C. in water.

The following examples describe the production and use of ribonuclease resistant RNA, illustrate the degree to which the reRNA can be protected from ribonuclease activity, and applications of the invention.

EXAMPLE I

Production of Armored RNA™ and Use of Armored RNA™ to Quantify HIV

1. Construction Of Armored RNA™.

The Armored RNA™ standard is a modified version of the RNA bacteriophage MS2 which contains only the Maturase and Coat Protein genes. A full-length cDNA clone of the RNA bacteriophage MS2 (pMS27) contains all the genes necessary to produce wild-type, infectious MS2 bacteriophage (Shaklee, 1990).

A fragment of DNA was synthesized from pMS27 by PCR™ encoding the Maturase and the Coat Protein of MS2 using the primers 5' CCTTTCGGGGTCCTGCTCAACTT 3' (sense primer SEQ ID NO: 1) and 5' GATTAGATCTGAGTTGAACTTCTTTGTTGTCTTC 3' (antisense primer SEQ ID NO: 2). A BglII restriction sequence was incorporated into the antisense primer to mediate the cloning of this PCR™ product into the expression vector pSE380 (Invitrogen Corporation). The PCR™ product was purified using the GeniePrep™ (Ambion, Inc.) and eluted from the glass fiber pad with 70 µl of water- GeniePrep™ is a DNA isolation kit that purifies plasmid DNA based on the common alkaline lysis procedure (Bimboim, 1983). The PCR™ fragment was digested with Nco I and Bgl II. Ten µl of 10× React 3 Buffer (BRL; 0.5M Tris[pH 8.0]; 0.1M $MgCl_2$; 1 M NaCl) 20 µl water and 3 µl of Nco I and Bgl II were added to the purified PCR™ product and incubated 37° C., 2.5h. An Nco I site is a naturally occurring sequence within the MS2 genome located just 5' of the start codon for the Maturase gene. The digested PCR™ product was again purified with GeniePrep™ (Ambion, Inc.) and eluted with 70 µl of water.

The digested PCR™ fragment was ligated into the Nco I and Bgl II sites of vector pSE380. pSE380 previously digested with Bgl II and Nco I was combined with the Bgl II and Nco I digested PCR™ product in a 1× Ligation Buffer (50 mM Tris [pH 7.8]; 10 mM $MgCl_2$; 10 mM DTT; 1 mM ATP; 0.025 mg/ml acetylated BSA, Ambion, Inc.) with T4 DNA Ligase (Ambion, Inc.). The ligation reaction was incubated at room temperature (~21° C.), 4 h. Ligated product was transformed into competent E. coli strain DH5α cells and then spread onto $Cb_{100}$-LB plates, 37° C., 16 h. Some of the resulting colonies were picked, grown in $Cb_{25}$-LB medium, the plasmid DNA isolated using GeniePrep™ (Ambion, Inc.) and then screened for a DNA insert with the same size as the PCR™ product by digesting the DNA with Nco I and Bgl II. The pSE380 vector contains the E. coli RNA Polymerase terminator sequence $rrnBT_1T_2$, 3' of the multiple cloning site, positions 709 to 866.

The resulting construct is named pAR-1. SEQ ID NO:3. Both bacteriophage genes are downstream of the strong trc promoter which is regulated by the lacI protein expressed by pSE380. The Operator sequence (pac site) is present in the Nco I/Bgl II fragment just downstream of the Coat Protein sequence. A truncated version of the Lysis gene is also present but the peptide encoded is not an active form of the protein. pSE380 encodes lac $I^q$, the superrepressor, which is inactivated in the presence of IPTG. Thus, transcription of the bacteriophage genes is down-regulated until IPTG is added to the culture medium and the trc promoter is activated. Transcription is terminated by the $rrnBT_1T_2$ terminator sequence.

The Maturase protein, the Coat Protein and the RNA which encoded these proteins were used for the production of the stable, bacteriophage-like Armored RNA™ particle. The Maturase protein is hypothesized to be an important component of Armored RNA™ that is hypothesized to stabilize the bacteriophage-like particle and endow additional protection for the RNA contained within the bacteriophage like particle. Therefore, many preferred embodiments of the invention will include the Maturase protein. There is a binding site for Maturase protein within the Maturase coding sequence (Shiba, 1981). The Maturase binding site was hypothesized necessary to be included in the reRNA as sequence which contributed to the packaging of the reRNA. The Coat Protein is an important component because it makes up the bulk of the bacteriophage particle. It was hypothesized unnecessary to include the Lysis gene or the Replicase gene because neither gene is involved in packaging. The Replicase is not needed because *E. coli* RNA Polymerase transcribes from plasmid DNA the RNA sense (+) strand encoding Maturase and Coat Protein once transcription is induced. However, as mentioned previously, it may not be necessary to have the genes for the Maturase and Coat Protein in cis with the RNA standard. They might be supplied in trans from another vector or even incorporated into the *E. coli* chromosome.

Armored RNA™ was produced using the pAR-1 recombinant plasmid. *E. coli* strain DH5α harboring this plasmid were grown overnight, 200 rpm, 37° C. in LB medium (10 g/liter tryptone, 5 g/liter yeast extract, 10 g/liter NaCl in water, pH 7.0–7.5) with 25 µg/ml carbenicillin ($Cb_{25}$). 0.2 ml of the overnight culture was used to inoculate 2 ml of fresh $Cb_{25}$-LB medium and incubated 1.5 h, 37° C., 200 rpm. Expression was induced by adding IPTG to 1 mM and incubating 3 h, 37° C., 200 rpm.

The cells were pelleted and then resuspended in 0.25 ml of 5 mM $MgSO_4$: 0.1 M NaCl: 50 mM Tris (pH 8.0) (Sonication Buffer). The cells were sonicated (Branson Sonifier 450) with the small sonication probe 50% duty cycle, unit 5 power for 5 pulses of the probe. The sonicate was iced 1 min and then the sonication step was repeated. The sonicate was centrifuged to pellet the cell debris. 20 µl of supernatant was incubated with 100 units of *E. coli* RNase 1 and 2 units of bovine pancreatic DNase 1, 37° C., 40 min, to eliminate *E. coli* RNA and DNA. After nuclease treatment, 15 µl of supernatant was electrophoresed on an agarose gel in TBE buffer and stained with Ethidium Bromide to assay for Armored RNA™.

The Armored RNA™ had a mobility of a 900–1000 base pair double stranded DNA fragment as compared to two different DNA size standards (lambda DNA digested with HindIII and pUC19 plasmid DNA digested with Sau 3A) which were also run on the gel with the Armored RNA™. The mobility was very similar to the wild-type MS2 bacteriophage mobility. Treatment of Armored RNA™ with DNase or RNase did not affect their intensity of staining or their electrophoretic mobility. Ribonuclease 1 (100 units; Ambion, Inc.) and DNase 1 (2 units; Ambion, Inc.) were added separately or together to 20 µl of the Armored RNA™ supernatant. The supernatant was incubated at 37° C. with these enzymes, 40 minutes and then fractionated on an 0.8% agarose gel in TBE buffer. Although the high molecular weight *E. coli* genomic DNA and the *E. coli* RNA were digested by the appropriate enzymes, there was no change to the signal of the Armored RNA™ except that it became more intense and resolved because presence of the *E. coli* nucleic acids in the supernatant tended to smear the signal of the Armored RNA™. However, the nucleases did degrade the genomic DNA and the host RNA.

Cells which were uninduced synthesized some Armored RNA™ but much less than the uninduced cells. Two cultures of pAR-1 in *E. coli* were grown to mid-log phase $Cb_{25}$-LB. One culture was then induced with 1 mM IPTG and the other was not. Both cultures were grown for another 3 h, 37° C., 200 rpm and then cultures were assayed for Armored RNA™ production. As assayed by gel electrophoresis and Ethidium Bromide staining, more Armored RNA™ was synthesized in the induced cells than in the uninduced. Cells were also induced for 16 h and this protocol resulted in the production of more Armored RNA™ than the 3 h induction.

The ribonuclease resistance of the Armored RNA™ containing the 1.7 kb truncated bacteriophage RNA indicates that the full length 3.6 kb of the MS2 bacteriophage genome is not required for the production of Armored RNA™ particles.

2. Construction of an Armored RNA™ HIV Standard pAR-1 served as the backbone for the creation of a quantitative HIV RNA standard compatible with the Amplicor™ HIV Monitor™ kit (Roche Diagnostic Systems). This study shows one example of how Armored RNA™ can be employed.

The QS RNA is the naked RNA standard in the Amplicor™ HIV Monitor™ test. The QS RNA encodes a conserved sequence of the gag gene from HIV but also contains a 26 bp substitution of randomized sequence. This random sequence is used to distinguish the wild type HIV amplicon from the QS amplicon since the HIV RNA and the QS RNA are co-amplified in the Monitor test.

RT-PCR™ was applied to the naked QS RNA to produce a DNA fragment encoding the QS sequence and contained Bgl II and KpnI restriction sites. The primers used were 5' GATTGGTACCTGCTATGTCAGTTCCCCT-TGGTTCTCT 3' (SEQ ID NO: 4) and 5' GATTA-GATCTAAGTTGGAGGACATCAAGCAGC-CATGCAAAT 3' (SEQ ID NO: 5). These primers correspond to the SK431 and SK462 primers respectively used in the Monitor kit (Mulder, 1994) except that a Kpn I sequence was added to the SK431 primer and a Bgl II sequence was incorporated into the SK462 primer. The QS PCR™ product was digested with Bgl II and Kpn I and ligated into the Bgl II and Kpn I sites in pAR-1 creating the recombinant plasmid, pAR-2 SEQ ID NO:6. DNA sequence of the Nco I/Kpn I fragment of pAR-2.

An Nco I/Kpn I fragment containing the Maturase, the Coat Protein and the QS RNA sequence was cloned into the Nco I/Kpn I restriction sites of the expression vector, pSE380 (Invitrogen Corp.) to produce pAR-2, SEQ ID NO:6. The important regions of the insert include: Nco 1(1>6), Bgl II(1713>1718), Kpn I (1862>1867), Maturase coding sequence (53>1231), Coat Protein coding sequence (1258>1647), Lysis Protein (1601>1711), the Capture Sequence within the QS sequence (1757>1782), the QS Amplicon region (1720>1861), SK462 primer (1720>1749), SK431 primer (1861>1835), Maturase Binding Site (311>337), and Operator sequence or pac site (1667>1687). SEQ ID NO:6.

pAR-2 in *E. coli* was induced with 1 mM IPTG in $Cb_{25}$-LB at mid-log phase for 3 h, 37° C., 200 rpm. The induced cells were pelleted and then sonicated in the Sonication Buffer used for the AR-1 particles. Then cell debris was pelleted by centrifugation. The sonicate supernatant was incubated with RNase 1 (5 units/µl) and DNase 1(0.1 units/µl), 37° C., 30 minutes and then fractionated on an agarose gel and visualized by Ethidium Bromide staining. The AR-2 particles were detected as a fluorescent band migrating at about 900 base pairs as compared to the DNA markers run on the same gel.

The AR-2 sonication supernatant containing the AR-2 particles was incubated under the same conditions as above with RNase 1 and DNase 1 except that the incubation was for 16 h. Another sample of AR-2 was incubated 16 h, 37° C. but nucleases were not added. These samples were fractionated on an agarose gel and compared to the AR-2 preparation which was stored at 4° C. The AR-2 signal was strongest in the sample which was treated with the nucleases because the nucleases degraded the nucleic acids which were masking the AR-2 signal.

The AR-2 were also isolated from culture supernatant. pAR-2 transformed *E. coli* were induced with 1 mM IPTG, 16 h in 50 ml of $Cb_{50}$-LB medium. Inoculation and induction were simultaneous. 0.4 ml lysozyme (50 mg/ml) was added to the culture and incubated 37° C., 200 rpm, 1 h followed by the incubation of the cell culture with 0.4 ml of 1-bromo-3-chloro-propane 37° C., 200 rpm, 10 min. The cell debris was pelleted by centrifugation in an SS34 rotor, 4° C., 9000 rpm, 10 min. The culture supernatant was transferred to fresh tubes and 0.015 ml of 1-bromo-3-chloro-propane was added. The culture supernatant was stored at 4° C. 0.015 ml of the culture supernatant was fractionated on an agarose gel and detected by ethidium bromide staining and UV fluorescence. AR-2 were detected in the supernatant as well as genomic DNA from *E. coli*. However, unlike the AR-2 isolated from *E. coli* cytoplasm, this AR-2 preparation did not contain detectable *E. coli* RNA. A 0.5 ml prep of AR-2 from the spent growth medium was treated with 10 units of DNase1, 37° C., 70 min. As assessed by gel electrophoresis, DNase1 completely degraded the host DNA but did not affect the AR-2.

0.02 ml of the AR-1 and AR-2 particles isolated from *E. coli* cytoplasm by sonication, were treated with 2 units DNase 1 and 100 units RNase 1, 37° C., 2 h and then 21° C., 16 h to degrade all host *E. coli* RNA and DNA. The AR preps were subjected to single tube RT-PCR™ using primer pairs specific for the QS amplicon, SK431 and SK462 (Mulder, 1994), and specific for the MS2 bacteriophage sequence, MS2-1 and MS2-2. The Armored RNA™ preps were diluted 10, 100 and 1000 fold in PBS. RT-PCR™ was performed with 1 µl of each of the Armored RNA™ dilutions using SK43 1/SK462 and MS2-1/MS2-2 primer pairs. Prior to the reverse transcription step, the Armored RNA™ preps were incubated at 95° C., 5 min to disrupt the protective protein coat of the Armored RNA™. The RNA was cooled on ice in the presence of the primers and then incubated with 100 units MMLV-RT, 42° C., 1 h. 2.5 µl Taq polymerase was added, followed by PCR™. The PCR™ products were fractionated by gel electrophoresis. Only the AR-2 generated the expected PCR™ product of 142 bp with the SK primers whereas the AR-1 and AR-2 generated a 411 bp product using the MS2 primers. These results were consistent with the AR-2 particles containing the QS RNA target and an MS2 RNA target while the AR-1 only contain the MS2 sequence.

Of course, the above protocol can be modified to produce almost any RNA standard by cloning the DNA sequence (encoding the RNA sequence of interest) into a recombinant plasmid such as pAR-1. SEQ ID NO:3. This plasmid encodes the Maturase, the Coat Protein and the Operator sequence and there are many convenient restriction enzyme sites immediately downstream (3') of the Bgl II restriction site of pAR-1. These restriction sites are the same restriction sites originally encoded in the multiple cloning site of pSE380, from nucleotides 396 to 622. Thus, DNA fragments may be synthesized chemically for cloning into pSE380. Alternatively, PCR™ or RT-PCR™ may be used to synthesize long DNA fragments (>100 bp) using primers which introduce restriction sites at both termini of the DNA fragment. The PCR™ DNA fragments may be digested for cloning into pAR-1.

An advantage of using the larger gene fragments is that PCR™ primers to different regions of these genes may be used with a single Armored RNA™ standard and it is not necessary to construct a different Armored RNA™ standard for each PCR™ primer pair that might be used. If large fragments of HIV RNA sequence (1 to 3 kb) are packaged into Armored RNA™, then the user has the option of using a variety of primer pairs for performing RT-PCR™. This type of construct may more readily conform to the primer pairs that the researcher is currently using and he would not need to change primer pairs in order to use the Armored RNA™ standard. The user is not limited to just one set of primer pairs as when using, for example, the short 142 base pair region used in the HIV monitor assay.

Of course, the HIV sequences may contain modifications from the wild-type sequence which will allow the standard sequence to be distinguished from the wild-type for the purpose of using the Armored RNA™ in competitive PCR™ as quantitative standards. Such modifications include insertions, deletions and restriction enzyme sequences.

It is not known what is the maximum limit of non-bacteriophage RNA can be packaged as an Armored RNA™. However, the full length genome of MS2 is ~3.6 kb and pAR-1 encodes only ~1.7 kb of the MS2 genome. Therefore, it is very likely that as a minimum, at least 2 kb of non-bacteriophage RNA sequence can be encapsidated as Armored RNA™ and possibly more if the Maturase and Coat Protein genes are supplied in trans.

3. AR-2 used as a Quantitative RNA Standard for HIV

In the Amplicor™ HIV Monitor™ test, the naked QS RNA standard is added to the Lysis buffer just prior to using the Lysis buffer for isolating the HIV RNA from plasma or serum. It is in this manner that the QS RNA is added to the plasma sample and that the HIV RNA and the QS RNA are co-purified. After isolation, the RNA is subjected to RT-PCR™ using Tth DNA polymerase which functions as a reverse transcriptase and a heat stable DNA polymerase. After RT-PCR™, the PCR™ products are incubated in the wells of an ELISA plate which contain oligonucleotides (capture probes) immobilized to the well bottoms. One set of wells has an oligonucleotide sequence which is complementary to the wild-type sequence of HIV. The other capture probe recognizes the unique sequence in the QS amplicon. Thus, the HIV capture probe hybridizes to the HIV amplicon while the QS capture probe hybridizes to the QS amplicon which result from the RT-PCR™ co-amplification. After hybridization, the amount of amplicon hybridized is detected enzymatically and calorimetrically using horse radish peroxidase. In the standard assay format recommended by the manufacturers, about 60 to 80 copies of the QS RNA standard are added to each sample for analysis, depending on the kit lot number.

To test Armored RNA™ in the Amplicor™ HIV Monitor™ test, the naked QS RNA, and the concentrated AR-1 and the AR-2 were subjected to the Amplicor™ HIV Monitor™ test. The QS RNA, AR-1and AR-2 were added to the Lysis buffer, the RNA was isolated and then subjected to the RT-PCR™ procedure. The PCR™ products were S15 detected on assay plates. The QS RNA produced the expected signal, the AR-1 were negative whereas the AR-2 produced a signal so strong that it was off-scale. Once the concentrated AR-2 prep was diluted 30 million fold, the signal became comparable to the QS RNA standard. The AR-2 prep was diluted by 30 million to produce a stock of Armored RNA™ which was the equivalent of 8,000 copies of QS RNA per milliliter. 10 µl of this AR-2 stock produced the same signal in the Amplicor™ HIV Monitor™ assay as the recommended amount of the naked QS RNA standard provided with the kit.

The AR-2 were diluted in water and stored at 4° C. over a period of several months. The diluted AR-2 were calibrated to produce a signal similar to the QS RNA in the Amplicor™ assay. Numerous Amplicor™ assays have been performed with the same diluted stock of AR-2. During a 38 day period, there has been no detectable decrease in the signal produced with the AR-2, highlighting the durability of these RNA standards (FIG. 1). This result is remarkable considering that this AR-2 stock was a crude preparation from *E. coli* and contained ribonucleases.

4. Durability of Armored RNA™ compared to naked RNA

One advantage of Armored RNA™ is that rather than adding the Armored RNA™ standard to the lysis solution prior to the lysis procedure, the Armored RNA™ standard may be added to the plasma or serum sample prior to RNA isolation, thus minimizing pipetting error in the assay. Armored RNA™ withstands plasma/serum nucleases very well compared to naked RNA.

10 µl RNA purified from AR-2 (about 5000 QS RNA equivalents), and intact AR-2 (about 500 QS RNA equivalents) were each added to 0.2 ml of normal human serum and incubated, 21° C. for 0 sec, 15 sec, 30 sec, 1 min, 5 min, 15 min, 1 h, and 4 h. The incubations were stopped by the addition of 4M guanidine thiocyanate, and 1% Sarkosyl solution and the RNA was extracted from the serum according to the method of Chomczynski (1987). Fifty microliters of a purified RNA preparation was amplified by RT-PCR™ for 26 cycles using the SK431/SK462 primer pair. The PCR™ products were quantified with a solid phase ELISA system (Mulder, 1994).

Figure 2:
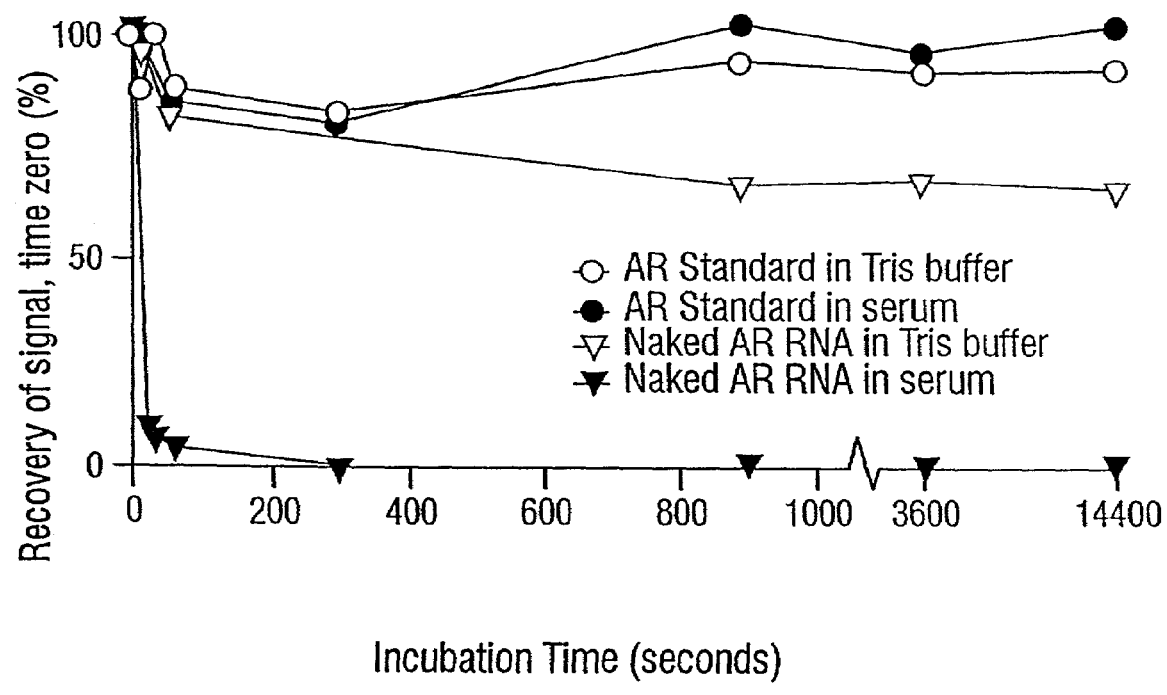
FIG. 2. The effect incubating intact AR-2 standards or naked AR-2 RNA in human serum. A defined amount of RNA either encapsidated as AR-2 (500 RNA equivalents), or as naked RNA isolated from AR-2 (5000 RNA equivalents) were incubated with human serum for increasing periods at room temperature (21° C.). As controls, the naked AR-2 RNA and the intact AR-2 standard were both incubated in parallel in Tris-buffer. Percent recovery is calculated as the $OD_{450}$ X dilution factor (DF) of the samples at time zero divided by $OD_{450}$ X DF at the end of each incubation multiplied by 100.

The AR-2 generated the same signal over the full time course while the signal from the purified RNA from the AR-2 disappeared almost immediately (FIG. 2). Clearly, the RNA in AR-2 was protected against plasma ribonucleases compared to the naked QS RNA.

EXAMPLE II

Use of Armored RNA™ to Quantify HIV

1. Use of Armored RNA™ Standard in the Amplicor™ HIV Monitor™ Assay

To perform the Amplicor™ HIV Monitor™ assay, a quantitative RNA standard of a known quantity is added to the patient's plasma sample and then RNA is isolated from the plasma. RT-PCR™ is performed on the RNA such that the standard and the HIV RNA are co-amplified using a single primer set. Both PCR™ products are measured and then the concentration of the HIV RNA is calculated using the signal obtained from the quantitative standard.

The Armored RNA™ standard containing the QS sequence (AR-2) is used in the Amplicor™ HIV Monitor™ test as follows. A known quantity of AR2 (-10 µl) is added to 0.2 ml of sample plasma. 0.6 ml of Lysis Reagent is added to the plasma sample containing the AR-2. The sample is mixed by vortexing 3-5 seconds and then incubated at room temperature 10 minutes. 0.8 ml of isopropanol is added to the sample tube and the sample is mixed by vortexing 3 to 5 seconds. The sample is centrifuged at maximum speed (~16,000× g) for 15 minutes. The supernatant is discarded without disrupting the pellet. 1 ml 70% ethanol is added, and the sample is vortexed 3 to 5 seconds followed by centrifugation for 5 minutes at ~16,000× g.

The pellet is resuspended in 0.4 ml of Specimen Diluent. 50 µl of the extracted sample is added to the MicroAmp tube containing the Master Mix and RT-PCR™ is performed using Tth Polymerase.

After amplification, 0.1 ml of Denaturation Solution is added to the amplicons. 0.1 ml of Hybridization Solution is placed into each of well of the Microwell Plate (MWP) used for detection of the amplicons. 25 µl of the denatured amplicon is added to the first well and 1:5 dilutions are performed using 25 µl in the next 4 consecutive wells such that there are dilutions of 1:5, 1:25, 1:125, 1:625 and 1:3125 for the detection of the HIV amplicon. Dilutions of 1:5 and 1:25 are made in the appropriate wells for the detection of the QS amplicon. The MWP is incubated for 1 hour at 37° C.

The wells are washed 5 times with Working Wash Solution and then 0.1 ml of AV-HRP is added to each well and incubated 15 minutes, 37° C.

The MWP is washed 5 times with the Working Wash Solution. Then, 0.1 ml of the Working Substrate is added to each well and the MWP incubated 10 minutes, in the dark, at room temperature. 0.1 ml of Stop Solution is added to each well and the optical density is measured at 450 nm. The concentration of the HIV in the plasma is calculated based on the signal obtained from the known concentration of the QS standard added to the patient plasma.

Besides using Armored RNA™ as a substitute for the naked QS RNA standard in the HIV Monitor™ assay, Armored RNA™ may also be used as a positive control in the assay. A wild-type sequence of HIV compatible with the HIV Monitor™ test could be packaged in Armored RNA™ such that it behaves as if it were a wild-type HIV. In this embodiment, an Armored RNA™ HIV Positive control is added to normal plasma at a known quantity and is then processed as if it were a patient sample except that the user would expect to obtain a certain pre-determined value in the assay. This standard would be used to demonstrate to the user that the assay was functioning properly.

2. Modified Amplicor™ HIV Monitor™ Test Procedure Well Suited to Armored RNA™

To increase the sensitivity of detection for HIV in the Amplicor™ assay, a procedure was developed in which the HIV virions are pelleted by high speed centrifugation from the plasma sample. Thus, 1 ml of plasma can now be assayed instead of the conventional 0.2 ml which the assay has used. This procedure should theoretically increase the sensitivity 5 fold, if the centrifugation step pellets 100% of the HIV virion. This protocol is only useful as a qualitative assay for HIV.

In this new procedure, the naked QS RNA would not be an optimal standard. It cannot be added to a plasma sample due the ribonucleases in the plasma which would degrade it and the naked QS RNA would not pellet by centrifugation with the HIV virions. Thus, when the plasma is removed after centrifugation, there is no control for loss of the HIV pellet. Armored RNA™ may be added to the plasma prior to centrifugation. It should pellet similarly to the HIV. Thus any loss of the pellet would be reflected in an equal loss in signal obtained from the Armored RNA™ standard.

Importantly, the use of Armored RNA™ standards can convert the centrifugation protocol from a qualitative assay to a quantitative assay.

3. Use of Armored RNA™ in Other Assays

Of course, the invention is not limited to a single, exemplary assay. There are other RNA based assays for HIV including: NASBA which is based on isothermal amplification (van Gemen, 1994; sold by Organon Teknika); the branched DNA assay developed by Chiron; an assay by DiGene in which an antibody recognizes a DNA/RNA duplex; and transcription mediated amplification, a technology similar to NASBA developed by Gen-Probe. For each of these assays, one skilled in the art can construct an Armored RNA™ standard containing appropriate sequence(s) to function appropriately as a quantitative standard.

The HIV NASBA assay uses three different quantitative RNA standards. The sequences of these standards are available in van Gemen (1994). Each of these NASBA standards could be cloned into pAR-1 in the same manner that the QS sequence was cloned into pAR-I to produce Armored RNA™ standards for the NASBA assay. RT-PCR™ may be used to amplify each of the standards for cloning into pAR-1.

The branched DNA assay by Chiron uses a single stranded DNA as the RNA standard. It encodes the gag and pol genes of HIV strain SF2. The sequence for this strain of HIV is available from GenBank, Accession number K02007. This HIV standard sequence is ~3 kb and may be too long for its full length to be packaged using pAR-1 as the vector for Armored RNA™ synthesis. It may be necessary to use a different construct which may permit longer sequences to be packaged. One such Armored RNA™ composition would be comprised of Maturase protein, Coat Protein and a reRNA coding Coat Protein, Operator site(s) Maturase Binding Sites and the HIV sequence encoding gag and pol. The Maturase would be encoded on another plasmid provided in trans. In this construct, the deletion of the Maturase Coding sequence from the reRNA may permit for the packaging of more non-bacteriophage sequence.

EXAMPLE III

Use of Armored RNA™ in a HIV Gel-Based Assay

An Armored RNA™ may be used as an external quantitative standard. A fragment of the HIV genome such as that region bounded by the SK431 and SK462 primers or some other region such as sequence encoding the pol gene can be cloned into the pAR-1 backbone. This construct can be used to synthesize Armored RNA™ in which the entire length of the cloned HIV fragment is wild-type HIV sequence. Such an assay does not require a unique capture sequence, because each amplicon is detected on an acrylamide or agarose gel either by ethidium bromide staining or by labeling the PCR™ product with $^{32}$P incorporation and autoradiography. A standard curve is generated by introducing known amounts of the HIV sequence in to the RT-PCR™ assay and then quantifying the amount of product generated on a gel. Actual copy numbers for test samples may then be derived using the standard curve. The Armored RNA™ is calibrated and used in RT-PCR™ reactions as if it were actual HIV. The PCR™ fragments may be fractionated either by agarose or acrylamide gel electrophoresis and quantified by ethidium staining or radioactivity. Standard curves may be generated by processing plasma containing different concentrations of the Armored RNA™. The standard curve may then be used to calculate the titers of patient samples by interpolation.

EXAMPLE IV

Use of Armored RNA™ as a Non-Infectious Standard

Armored RNA™ may be used as non-infectious proficiency standard (a certified and well characterized plasma, serum or urine based product designed for the validation of the accuracy of the instrumentation and methods of an assay) or as positive controls. Gene fragments of a standard HIV strain are cloned into the Armored RNA™ recombinant plasmid to produce a family of Armored RNA™-HIV standards. These include the pol and gag genes, which are well conserved in HIV. The inventors envision AR-gag, AR-pol and AR -gag/pol RNA standards. These Armored RNA™ standards are quantified precisely and then can be used as external quantitative standards for RT-PCR™ or other amplification techniques. The Armored RNA™ may be added directly to plasma and used as such, or the AR-HIV RNA may be extracted from the purified Armored RNA™ in a standard salt buffer such as PBS or Tris:NaCl.

EXAMPLE V

An Armored RNA™ Standard Used in an HCV Assay

Armored RNA™ technology will be useful in creating RNA standards for viruses that are difficult or hazardous to culture. For example, hepatitis C virus (HCV) cannot be reliably grown in tissue culture, whereas an Armored RNA™ standard for HCV could easily be constructed and produced. HCV isolates can be classified into 6 distinct genotypes based on the nucleotide sequence variation in the core gene region or the NS5 region (Simmonds, 1994). Genotype-specific Armored RNA™ standards can be constructed to serve as controls in assays designed to identify specific HCV genotypes and HCV subtypes such as 1a, 1b, 2a, 2b, 2c, 3, 4a, 4b, 5a, and 6a. Genotyping strategies have been based on sequencing, RFLP analysis, PCR™-based assays with type-specific primers, and a line probe assay (van Doom, 1994). For example, the latter assay involves the differential capture of a 244 basepair product that is generated from primers at positions 56 through 299 of the HCV genome. The amplicon used to identify each of these strains is short enough that it is straightforward to chemically synthesize the DNA fragments to be cloned into pAR-1 and thus circumvent the need to handle infectious material in order to clone these genotype sequences. Protected recombinant RNA from human serum samples could be constructed using primers KY80s5 (5'GCA-GAAAGCGTCTAGCCATGGCGT) (KY80-SEQ ID NO: 7) and KY78 (5'CTCGCAAGCACCCTATCAGGCAGT) (KY78-SEQ ID NO: 8). By using samples with defined genotypes, genotype-specific recombinant standards could be constructed. Armored RNA™ standards for HCV may be constructed using a strategy similar to the one for the HIV standard. These RNA standards may be used either as positive controls for strain typing or quantitative RNA standards.

For strain typing, the primers KY78 and KY80 may be used to synthesize DNA fragments by RT-PCR™ from different HCV strains. These strain specific DNA fragments may be cloned into pAR-1 such that RNA encoding strain specific HCV is packaged as Armored RNA™. As well, strain specific sequences have also been documented for HCV between positions 56 to 299 of the HCV genome. It is possible to chemically synthesize these sequences and clone them directly into pAR-1 for packaging. This method would circumvent the need to handle infectious HCV. Thus, in the differential capture assay, each strain specific PCR™ product of HCV would hybridize to a unique capture probe immobilized to the bottom of a plastic well.

To create a quantitative HCV Armored RNA™ standard, the amplicon produced by the KY78 and KY80 primers could be modified by substituting in the same capture sequence used in the QS sequence for HIV or some other 25 to 30 base pair region within this amplicon may be randomized so that it can be differentiated from the wild-type amplicon. The substitution may be performed by one skilled in the art by PCR™. As in the Amplicor™ HIV assay, the HCV quantitative standard would be co-amplified with the wild-type RNA. The HCV Armored RNA™ standard would be added to the sample plasma prior to the RNA isolation step.

EXAMPLE VI

Collection Tubes Containing Pre-Determined Quantity of Armored RNA™

Owing to the durability and stability of Armored RNA™, it may be aliquoted into blood collection vessels or other fluid collection vessels in a pre-determined quantity. The Armored RNA™ may then be freeze dried for long term storage at room temperature or left in buffered salt solution and stored at 4° C. or even room temperature (~21° C.). At the time of use, blood is drawn into the collection tube with the Armored RNA™ standard. The blood sample is inverted many times to thoroughly mix the Armored RNA™ standard into the sample. The blood may be stored as usual until it is subjected to the quantitative assay. This strategy precludes the need to add an RNA standard to the plasma sample prior to the RNA isolation from plasma. It would control for the partitioning of the viruses between the blood cells and the plasma or serum fractions.

Further, multiple Armored RNA™ standards may be included in the collection tube such as an HIV and an HCV standard so that the quantification for one or both pathogens may be performed.

EXAMPLE VII

Use of Armored RNA™ in Veterinary Diagnostics

Domestic animals are often infected with RNA viruses. For cats, retroviruses represent the largest cause of premature death other than automobile accidents. Up to one-third of the cats exposed, are infected with Feline Immunodeficiency Virus (FIV) and Feline Leukemia Virus (FeLV) (Essex, 1995), similar to their human counterparts, HIV and human T cell lymphotropic virus-type 1 (HTLV). One skilled in the art could construct Armored RNA™ standards for FIV and FTLV, similar to the AR-2 standard described for HIV. These standards may be used for quantification or as positive controls in FIV and FeLV diagnosis by RT-PCR™.

EXAMPLE VIII

Use of Double Stranded RNA Bacteriophage

Bacteriophage φ6 is a double stranded RNA bacteriophage in which it is possible to package in vitro, non-bacteriophage RNA to produce viable, genetically stable bacteriophage (Qiao, 1995). It has been demonstrated that the RNA in these bacteriophage are protected from ribonucleases. One skilled in the art may produce recombinants containing a standard RNA sequence so that the recombinant bacteriophage φ6 may act as quantitative standards for human infectious, double stranded RNA viruses such Rota Virus and Vesicular Stomatitis Virus. It is possible following the teachings of this specification and the art to develop a packaging system with bacteriophage φ6 whereby the packaged material is not viable/infectious, similar to the Armored RNA™ standards.

A double stranded non-infectious RNA bacteriophage may have applications as a therapeutic. Double stranded RNA is known to stimulate cells to produce important immunomodulators which act as anti-viral agents such as interferon (Stiehm, 1982).

EXAMPLE IX

Quantification of a Cellular mRNA

One skilled in the art can use an Armored RNA™ standard for the quantification of an mRNA expressed by a cell. In studies to determine the induction or repression of specific mRNAs over a period of time, an equal number of cells could be harvested at each time point before and after the cells had been exposed to the treatment under investigation. The Armored RNA™ standard would be added in a known quantity to each time point prior to the purification of the RNA from the cells. The Armored RNA™ standard could then be used to quantify the amount of a target mRNA such as a cytokine, a cell cycle gene or an oncogene. The Armored RNA™ standard would be constructed containing the same primer pair binding sites as the target gene. The Armored RNA™ standard could be differentiated from the wild type RT-PCR™ product by altering the sequence between the primers pairs using one of the methods discussed above such as incorporating a restriction site or a deletion. One skilled in the art can produce amplicons which have insertions, deletions or substitutions as compared to the wild-type sequence. There are several different methods available for site-directed mutagenesis, each of which involve oligonucleotides which encode the desired sequence of the standard.

Standards containing deletions, insertions and restriction sites are often preferred for gel based assays because they are easily differentiated from the wild-type amplicon by fractionation on an agarose or acrylamide gel. For each of these standards, a size difference of about 10% is often used. PCR™ may be used to generate any of these standard sequences. To generate a deletion mutant, an oligonucleotide is synthesized which contains primer sequences as well as other amplicon sequence. The amplicon sequence and the primer sequence flank the sequence in the wild-type sequence which is to be deleted. When this oligonucleotide hybridizes to the wild-type, the sequence to be deleted is looped out and is not incorporated into the new DNA strand during polymerase extension. One skilled in the art may use similar strategy to create insertions and substitutions whereby one of the primers in a PCR™ reaction contains the desired mutation. Two such strategies are discussed in detail in Schneeberger (1996) and Hughes (1996).

EXAMPLE X

Preparation of Armored RNA™ Standards for Commercial Use

It is important that the Armored RNA™ standard is free of any host DNA or RNA which may affect quantification by RT-PCR™. To produce a homogenous lot of an Armored RNA™ standard, a crude extract would be prepared from the culture supernatant after a 16 h induction of the E. coli transformants (see EXAMPLE 1). This preparation is contaminated with the genomic DNA from *E. coli*. Contaminating RNA and DNA may be removed by adding RNase and DNase to the crude extract.

Traditionally, MS2 bacteriophage are purified by a CsCl gradient. They band tightly at a concentration of 1.45 g/cc (Pickett, 1993). Armored RNA™ may be purified by using a CsCl gradient procedure similar to the MS2 bacteriophage. After centrifugation, the Armored RNA™ band is pulled and then dialyzed against a salt buffer such 100 mM NaCl: 50 mM Tris (pH 7.5) or PBS. Armored RNA™ may be quantified by obtaining an $OD_{260}$ and an $OD_{260}$ which are used in the art to measure nucleic acid and protein concentrations, respectively. After a stock of Armored RNA™ has been made, it may be calibrated against a naked RNA containing the same amplicon. For example, Armored RNA™ standards may be calibrated against the naked QS RNA standard.

The nuclease treated crude extract of Armored RNA™ may be also purified by gel exclusion chromatography, using a resin such as Sephacryl S-200 (Pharmacia) (Heisenberg, 1966). Due to the large size of the Armored RNA™, they will run in the void volume while other protein and nucleic acid components will be retarded. Armored RNA™ in the void volume may be calibrated as above. It will be advantageous to couple several purification procedures to ensure that the Armored RNA™ is completely homogenous.

Large scale production of Armored RNA™ may be performed as follows. A 100 ml inoculum of *E. coli* harboring the pAR construct is grown to mid-log phase in $Cb_{25}$-LB medium. This inoculum is used to inoculate 1,000 ml of 1 mM IPTG- $Cb_{25}$-LB medium. The cells are incubated 16 h, 200 rpm, 37° C. One-ml of lysozyme (50 mg per ml) is added to the culture and incubated 37° C., 1 h, 200 rpm. The culture is pelleted by centrifugation. The supernatant contains Armored RNA™ particles and *E. coli* genomic and plasmid DNA. Contaminating RNA and DNA is degraded by adding $CaCl_2$ to the supernatant to 10 mM and the supernatant is then incubated with Micrococcal Nuclease (30 units/ml), 37° C., 1 h, 200 rpm. EDTA is added to 25 mM to chelate the $CaCl_2$ and stop the nuclease activity. The AR particles are precipitated with 50% Ammonium Sulfate, 4° C., 2 h. The precipitate is pelleted by centrifugation. The pellet is resuspended in 100 mM NaCl: 1 mM EDTA: 10 mM Tris (pH 7.5) (TSE buffer). 0.6 g of CsCl is added to every gram of AR2 solution. The CsCl is dissolved and transferred to a heat sealed ultracentrifugation tube for the 50.2 Ti rotor (Beckmann). The CsCl gradient is centrifuged at 45,000 rpm, 20 h, 21° C. The AR particles band about the middle of the centrifuge tube. The CsCl band is pulled with a needle and syringe, about 5 ml. The AR2 particles are finally passed over an Sephacryl S-200 resin in TSE buffer. The particles elute in the void volume. The number of AR2 particles may be determined using the extinction coefficient of 1 $OD_{260}$=0.125 mg/ml of MS2 bacteriophage and the molecular weight is $3 \times 10^6$. Based on this procedure, approximately $1 \times 10^{15}$ AR particles can be purified from one liter of culture.

Electron microscopy may be used to count the Armored RNA™ directly. This method has been used for quantifying HIV (Lu, 1993).

After purification, the Armored RNA™ may be stored at 4° C. or at room temperature. A biocide may be added to prevent bacterial or fungal growth in the standards. The Armored RNA™ is diluted to concentrations which are convenient for quantification.

EXAMPLE XI

Use of Other RNA Bacteriophage for Constructing Armored RNA™

There are 3 other genetically distinct groups of RNA coliphage and at least 2 other non-*E. coli* RNA bacteriophage, PP7 and PRR1 (Dhaese, 1979; Dhaese, 1980). These bacteriophage have Coat Proteins which are homologous in protein sequence to the MS2 Coat Protein (Golmohamrnadi, 1993). As with the MS2 phage, the cDNA of the Maturase and the Coat Protein of any of these bacteriophage could be cloned into an expression vector such as pSE380. These recombinant plasmids may act as vectors into which non-phage DNA sequence may be cloned. The transcript of the non-phage sequence would contain the Operator sequence and the Maturase binding sequence for these other bacteriophages such that the non-phage RNA sequence would be encapsidated with Coat Protein and Maturase of the appropriate strain specific phage. In this manner, Armored RNA™ may be composed of Coat Protein and Maturase from any of the RNA bacteriophage species. Similarly to the pAR-2 construct, induction would produce a reRNA which encodes Maturase, Coat Protein, Operator sequence(s), and the Maturase Binding sequence(s) of these other bacteriophages such that the non-bacteriophage RNA sequence would be encapsidated with the Coat Protein and Maturase of the appropriate strain specific phage.

EXAMPLE XII

Plant Virus Armored RNA™

Plant viruses can be used to prepare Armored RNA™. For example, TMV and Potyvirus can be used for this purpose.

1. Tobacco Mosaic Virus Packaging.

It is possible to package recombinant RNA (reRNA) using Tobacco Mosaic Virus (TMV) coat protein in *E. coli* (Hwang 1994a and Hwang 1994b). TMV is a filamentous virus composed of 2,100 of a 17 kDa coat protein that protects a 6.4 kb single stranded, positive sense genomic RNA against ribonucleases. TMV has been used as a model system for studying self-assembly of multimeric biological structures. Under the correct conditions, purified TMV coat protein and the gRNA will spontaneously assemble to form an infectious virus in vitro. As well, reRNA packaged in vitro with TMV coat protein is protected against ribonuclease digestion (Jupin et al., 1989).

The TMV gRNA has an operator-like sequence called the Origin-of-Assembly-Sequence (OAS) recognized by the coat protein to initiate assembly. The OAS is located at nucleotides 5112-5543 in the wild-type virus, 432 nucleotides in length. The OAS exists as a three stem-loop structure. The minimal length of the OAS required for packaging is 75 nucleotides, nucleotides 5444–5518.-The coat protein assembles faster in the 3' to 5' direction along the RNA than in the 5' to 3' direction.

In the TMV-*E. coli* packaging system, TMV coat protein was plasmid encoded and provided in trans to the reRNA to be packaged. (Hwang 1994a, Hwang 1994b, U.S. Pat. No. 5,443,969). reRNAs, containing a 5' open-reading frame and an OAS, of 1.6 kb (CAT-OAS RNA) and 2.8 kb (GUS-OAS RNA) were transcribed in *E. coli* from a second plasmid. Co-expression of the coat protein and the reRNA resulted in the packaging of the reRNA. The integrity of the reRNA packaged was assayed by RT-PCR™. Full-length CAT-OAS RNA was detected by RT-PCR™ but full-length GUS-OAS RNA was not detected.

2. Potyvirus Packaging.

Potyvirus is another example of a plant virus that can be used to produce Armored RNA™. Its coat protein has been expressed and assembled into capsids in *E. coli* (Zhoa, 1995). However, there was no mention of the RNA which may heave been packaged. Presumably, there must be an operator-like sequence as is found for MS2 and TMV. No reference has been found to such a sequence for Potyvirus. A reRNA could be packaged by this coat protein once its operator sequence was discovered.

To define the operator sequence in potyvirus, a systematic set of packaging Is experiments may be performed, similar to the experiments of Pickett and Peabody (1993). The potyvirus coat protein gene may be expressed from one vector in *E. coli*. Another vector may be used to transcribe different segments of the potyvirus genomic RNA in about 1 kb lengths. These sequences could be fused to a reporter sequence, that is, a known sequence common fused to each segment of the potyvirus genomic RNA. The reporter sequence may be as short as 20 bases. The potyvirus coat protein and the test sequences may be co-expressed in *E. coli* and the viral particles isolated. The RNA may be isolated from the particles and then the RNA assayed for the reporter sequence by one of a number of different methods such as RT-PCR™, Northern blotting, dot blotting, or RPA. Particles containing the reporter sequence would be candidates for containing the operator sequence. The operator sequence can be further defined by performing an iteration of the same experiment, further dividing the 1 kb candidate sequence into 250 base sequences. Once an operator sequence is identified, it can be used with potyvirus coat protein to package heterologous RNA sequences.

By employing a strategy like that used to make bacteriophage Armored RNA™, a recombinant RNA can be transcribed in *E. coli* composed of the potyvirus coat protein sequence, non-potyvirus sequence and the potyvirus operator sequence. This reRNA will be packaged specifically by the potyvirus coat protein because it contains the operator 5 sequence at the 3' end. In this system, the coat protein sequence and the operator sequence are in cis. Another alternative is to transcribe the coat protein RNA and the non-potyvirus RNA/operator RNA in trans. Such a trans system was used both with MS2 (Pickett and Peabody, 1993) and with TMV.

EXAMPLE XIII

Animal Virus Armored RNA™

Animal viruses can be used to produce Armored RNA™. An example of this is seen with regard to the alphavirus.

1. Alphavirus Packaging.

Alphaviruses are enveloped positive, single strand RNA viruses which infect is mammals, birds, and insects. Examples from-this virus family are Semliki Forest Virus (SFV), Sindbis virus, and Venezuelan Equine Encephalitis (VEE). Over the past ten years, these viruses have been adapted for the expression of recombinant RNAs and proteins in animal cells. (Frolov 1996 and U.S. Pat. No. 5,217,879).

The alphavirus particle has a single genomic RNA protected by 240 copies of basic capsid protein (C), surrounded by a lipid bilayer containing 240 E1E2 envelope glycoprotein heterodimers. Alphaviruses can infect a variety of cell types and may use more than one receptor to gain entry into a cell. The virus has an icosehedral symmetry. The genomic RNA is capped at the 5' end and it is organized such that the 5' end half encodes non-structural genes for RNA replication and the 3' half encodes the structural genes for packaging the RNA. There is a packaging signal sequence within the non-structural region of the genomic RNA required for efficient encapsidation.

Several strategies have been used to package reRNA using the alphavirus system. In one method, an infectious recombinant virus is produced in which the complete wild-type genomic RNA is maintained and the foreign sequence of interest is inserted 5' or 3' or the structural genes. Foreign RNA sequences up to 2 kb can be packaged. This method was used to package several foreign genes including bacterial chloramphenicol acetyltransferase (CAT) and a truncated form of the influenza hemaglutinin. Cells infected with these recombinant alphaviruses produced the encoded proteins.

Another strategy for the packaging of reRNA involves the production of non-infectious particles. In this system, the structural and non-structural RNAs are encoded in separate, distinct RNAs with the replicase sequence containing the packaging signal and the foreign RNA sequence. These two RNAs are co-transfected-into a cell. The replicase replicates both the non-structural and structural RNAs while the structural RNA generates the proteins which only package the non-structural/foreign gene RNA. These particles are non-infectious because the structural genes are not packaged with the non-structural genes. Using this method, it is estimated that at least 5 kb of foreign RNA can be packaged.

There are other variations of the above described packaging systems involving similar type strategies but most of them are designed to increase the protein expression of the foreign RNA sequence.

The alpha-particles will protect RNA from ribonucleases in much the same manner as the MS2 particles. It is to be expected that the reRNA will protected from ribonucleases because alphaviruses could not re-infect if their genomic RNA were susceptible to ribonucleases once it was packaged and the viruses were released from their host cell.

The alpha-particles may not be as heat resistant as bacteriophage Armored RNA™, because they have a different coat structure. The bacteriophage Armored RNAs may be the preferred choice for shipping purposes if alphaviruses are heat sensitive. However, any heat sensitivity would not be an insurmountable problem as particles could simply be shipped on dry or wet ice.

Because alphaviruses are physically very similar to HIV, they may be a better pelleting standard for ultra-sensitive assays. The alphaviruses have more in common with HIV and HCV structurally than with the bacteriophages. Thus, they may pellet by centrifugation more like the HIV and HCV they are supposed to mimic. Pelleting the viruses may be important in developing a good standard for an ultrasensitive assay. HIV in 1 ml of plasma can be concentrated by centrifugation and then the RNA is extracted from the viral pellet. Alphavirus particles may also accept longer foreign sequences than the MS2 system, because they have a larger genome than bacteriophage. Alphavirus particles should be stable in serum/plasma for time periods similar to HIV. Many of these viruses are transmitted through mosquito vectors. Therefore, the virus must survive exposure to plasma.

EXAMPLE XIV

Construction of Armored DNA

There are many well studied single- and double-stranded DNA bacteriophage which infect E. coli as well as a number of other bacteria. It is straightforward to clone DNA fragments into a single stranded bacteriophage such as M13 or into the double stranded bacteriophage k. These recombinant phage are readily purified and quantified by determining the plaque forming units. They may act as standards for PCR™ based assays for DNA viruses. For instance, a X recombinant bacteriophage containing a conserved DNA sequence of the human pathogen, the Herpes Simplex Virus may act as a double stranded DNA standard. It may be used as a quantitative standard or as a positive control.

EXAMPLE XV

Subtraction of rRNA from Total RNA

The Armored RNA™ may be used to synthesize large mass amounts of RNA which encodes the antisense sequence of 18S and 28S rRNA. Once the RNA has been isolated and purified, it can be labeled with photobiotin. The biotinylated RNA is added to total RNA in molar excess over the target 18S and 28S rRNA. The mix is heat denatured in a hybridization buffer promoting the formation of RNA hybrids and then allowed to cool to room temperature to encourage the formation of the duplex between the 18S and 28S rRNA with the biotinylated antisense RNA. After hybridization, streptavidin is added to the solution and binds to the biotinylated RNA. A phenol extraction partitions all the unbound streptavidin and biotin/streptavidin complexes into the organic phase. The 18S and 28S rRNA hybridized to the antisense biotinylated RNA also partitions into the organic phase. By this strategy, the 18S and 28S are subtracted from the total RNA. Since the molar quantity of 18S and 28S rRNA is very abundant in total, large quantities of antisense RNA would be required for this strategy. Armored RNA™ technology could provide as a means to provide a cheap source of RNA.

EXAMPLE XVI

Construction of RNA Size Standards

Mixtures of RNA of very discrete lengths are often used as RNA size standards for gel electrophoresis. These size standards are used often in Northern blotting to estimate the length of unknown mRNA species. In general, the RNA size standards range from 0.2 to 10 kilobases. The RNA in these standards are susceptible to ribonucleases and they are usually produced by in vitro transcription. Therefore, any of the methods described herein may be used to create ribonuclease resistant RNA size standards.

For example, a series of Armored RNA™ standards can be constructed, each containing an RNA of a different length. DNA fragments of different sizes would be cloned into pAR-1 to construct this series of size standards. The size range of the standards will be dependent on the RNA size limitation of the packaging system. After production, each of the Armored RNA™ size standards would be produced and quantified separately. The standards would be mixed so that the RNA of each of the standards are at the same mass concentration.

In a preferred embodiment, the mixed Armored RNA™ size standards will be added to a denaturing solution just prior to their use for gel electrophoresis in order to disrupt the RNA-protein complex. The denaturing solution may consist of an acid such as acetic acid, a detergent such as SDS or a chaotrope such as urea. The standards would be heated and then loaded on the gel. The advantage of this embodiment is that there is no chance for the RNA standards to be degraded until just prior to gel electrophoresis.

In another embodiment, the Armored RNA™ mixture is used as the stock solution from which to isolate the size standards. The RNA may be isolated using a common RNA isolation procedure such as by Chomczynski (1987).

Of course, it is also possible to isolate the RNA from each of the Armored RNA™ size standards separately and then mix the RNA afterwards.

Alternatively, it is possible to construct ribonuclease resistant chemically modified RNA size standards, which can be used as a single standard or in sets of mixed standards.

EXAMPLE XVII

Removal of the Non-Phage RNA from the Phage RNA

There are applications where a researcher may want an RNA which does not encode any phage sequence. All the Armored RNA™ compositions contain a reRNA which encodes some amount MS2 bacteriophage sequence. One skilled in the art may construct the RNA sequence so that the RNA sequence of interest is flanked by ribozyme sequences as demonstrated previously (Ferré-D'Amaré, 1996). The non-phage RNA may be encapsidated with the ribozyme sequences because these sequences are not very active in E. coli. After the RNA is isolated from the Armored RNA™, the RNA may be subjected to buffer conditions which produce optimal ribozyme activity. After ribozyme cleavage, the RNA fragment of interest may be purified by gel electrophoresis or HPLC.

Another method previously used by others involves using Ribonuclease H which cleaves RNA at RNA/DNA duplexes (Lapham, 1996). Oligonucleotides complementary to regions flanking the desired RNA fragment are hybridized to the naked reRNA after it has been purified from the Armored RNA™ particle. This substrate is subjected to RNase H which will cleave the reRNA at the sites where the oligonucleotide has hybridized. DNaseI may be used after to digest all the oligonucleotides.

After purification, the RNA fragment may be capped with RNA guanyltransferase using GTP and SAM which may then be a suitable substrate for translation.

EXAMPLE XVIII

Use of Armored RNA™ to Deliver RNA In Vitro and In Vivo

Armored RNA™ technology may be used to deliver intact, full length RNA to cells in vitro and in vivo. Transfection of cells with RNA is performed with naked RNA which is susceptible to ribonucleases. Transient gene expression may be optimized by producing an RNA message as an Armored RNA™, to protect the RNA until it enters a cell. Upon entry in the cell, the protective Coat Protein may be removed by the cellular machinery. The use of a bacteriophage system to deliver intact RNA would be similar to a TMV system which was previously employed. A recombinant RNA was packaged in vitro using TMV Coat Protein and successfully delivered into plant cells and into frog cells (Gallie et al, 1987).

The RNA need not be capped for translation. An encephalomyocarditis virus or Polio translational leader sequence may be fused upstream of the coding sequence to promote the internal initiation of translation in vitro or in vivo (Elroy-Stein, 1989). This system is cap independent for translation. The Armored RNA™ may be mixed with DOTAP, Lipofectin, Transfectam or Lipofectamine to form cationic liposomes to optimize membrane fusion. Liposomes have been used successfully to increase the efficiency of RNA transfection with cells from tissue culture (Lu, 1994; Dwarki, 1993). As well, the Maturase or the Coat Protein could be genetically engineered so that either or both contain a peptide sequence which recognize specific cell surface receptors. These ligands would promote tissue-specific uptake of the Armored RNA™. Peptide sequences up to 24 amino acids can be inserted into the MS2 Coat Protein such that the recombinant Coat Protein will maintain its ability to assemble into capsids (Mastico et al., 1993). Peptide sequences which recognize cell-specific receptors could be incorporated into Coat Protein. The recombinant Coat Proteins would be used to package reRNA, in vitro or in vivo, into Armored RNA to produce a multivalent macromolecule which would recognize specific cell surface receptors. The multivalent property of the Armored RNA would confer a strong affinity for the cell surface receptor. The peptide receptor sequences could be derived using phage display technology (Barry, 1996; Pasqualini, 1996) or by using previously characterized peptide sequences (Hart, 1994).

An mRNA may be packaged in vivo by cloning the gene of interest, such as the CEA gene (associated with many different tumors and thought to be a tumor rejection antigen), into a vector such as pAR-1. The gene would be cloned immediately downstream of the Operator sequence in pAR-1. As well, the EMCV translation sequence would be cloned between the Operator and the CEA coding sequence. In this way, the CEA RNA may be translated without requiring a 5' CAP to enhance translation of the mRNA.

For in vitro transfection, the CEA-Armored RNA™ would be mixed with the tissue cultured cells, with or without forming liposomes before transfection. The liposomes may enhance fusion of the Armored RNA™ with the cells. Also, the CEA-Armored RNA™ may be microinjected into oocytes. The use of Armored RNA™ would forgo the requirement for the usual precautions in handling RNA. In these procedures, it is is expected that the Armored RNA™ would dissociate upon entering the target cell and release their packaged RNA so that it is available for translation.

In vivo, the Armored RNA™ may be injected into tissues by a variety of routes such as intravenous or intramuscular to produce the protective immune response. It would be desirable that the Armored RNA™ could be taken up by the appropriate immune cells to produce the strongest and most protective immune response. One skilled in the art could introduce the appropriate counter receptor (or ligand) sequence into the Maturase or Coat Proteins so that the Armored RNA™ would bind and be taken up by the strongest immunomodulators. This strategy would require prior knowledge about the some specific cell specific receptors on these immunomodulators so that they could be targeted appropriately.

If a one time vaccination is not enough to produce a protective immune response, then multiple immunizations may be required. In this case, the Armored RNA™ themselves may be immunogenic and would become less effective at transfection as the individual develops immunity to the Armored RNA™ itself Multiple vaccinations may involve using Armored RNA™ developed from RNA bacteriophage from several different serotypes. All of the Armored RNA™ vaccinations would contain the same protective mRNA, however, it would be packaged by phage capsids from different serotypes. For instance, the RNA coliphages are divided into serological groups I, II, III and IV. There are also the two strains of P. aeruginosa RNA bacteriophase. Thus, the CEA mRNA may be packaged in as many as 6 different Armored RNA™ and each would be used for each different immunization.

A capped mRNA may be encapsidated co- or post-transcriptionally. An mRNA with a 5' cap may be synthesized by using a cap analog nucleotide during in vitro transcription or an RNA transcript may be capped with RNA guanyltransferase using GTP and S-adenosyl methionine as substrates. After mRNA synthesis, the mRNA may be mixed with Coat Protein and/or Maturase to produce Armored RNA™. The mRNA may contain one or more Operator sequences and/or one or more Maturase Binding sites but they are not essential for the packaging of long RNA molecules. These Armored RNA™ synthesized completely by in vitro methodologies may be used for transfection into cells. Again, the Coat Protein may manipulated to express a ligand which will enhance the binding of the Armored RNA™ to the target cell and promotes its uptake and processing.

Recently, phage display technology was used to select for peptides which bound selectively to specific cell types in vitro (Barry, 1996) and in vivo (Pasqualini, 1996). Libraries of filamentous DNA bacteriophage displaying random peptide sequences were either panned over mouse fibroblast cells grown in culture or they were injected intravenously into mice and the bound bacteriophage were eluted from different organs. Panning over the mouse fibroblast cells resulted in bacteriophage clones which bound well to fibroblast, hepatoma, and mastocytoma cells but not to myoblast or macrophage cells. Intravenous injection into a mouse resulted in bacteriophage which bound selectively to brain tissue and to kidney. Peptides were synthesized based on the sequence derived from the bacteriophage which bound selectively to brain. These peptides were able to block the adherence of the bacteriophage to the brain capillaries.

These data suggest that Armored RNA™ can be developed into a delivery system for gene therapy or drug treatment which will target specific organs. Indeed, it has been demonstrated that filamentous bacteriophage displaying the peptide sequence RGD, which promotes binding to the cell surface receptor integrin, are internalized in human HEp-2 cells (Hart, 1994).

The Armored RNA™ may also be added to in vitro translation systems such as a rabbit reticulocyte extract. As stated earlier, capped, polyA mRNA may used if the reRNA is packaged post-transcription using an in vitro packaging system.

The Coat Protein or the Maturase could be modified to contain the biotinylation peptide sequence which leads to this peptide becoming biotinylated in E. coli. In this strategy, the Armored RNA™ would be coated on the surface with biotin molecules which are accessible to streptavidin. Streptavidin may be conjugated to ligands which recognize specific cell surface receptors. The ligand-streptavidin conjugate may be incubated with the Armored RNA™ to coat it with the streptavidin-ligand conjugate. The ligand-streptavidin-Armored RNA™ complex may be used to deliver the packaged RNA.

Antibodies to Armored RNA™ could be conjugated to receptor molecules as previously performed (Douglas et al., 1996). The Armored RNA™ particles would be pre-coated with an antibody-receptor conjugate thus conferring receptor specificity to the Armored RNA™. The Armored RNA™ Antibody Receptor complex would bind to a specific cell and then be taken into the cell.

Armored RNA™ may be made more effective as a delivery vector if the Armored RNA™ disassembles easily once it enters the cell. By using mutant forms of the Coat Protein in the Armored RNA™, it may be possible to produce less stable structures which may protect the encapsidated reRNA from ribonucleases but dissociates readily upon entry into a cell. Mutant forms of the Coat Protein have been studied which are less efficient at capsid assembly (LeCuyer, 1995) and have less thermal stability compared to the wild-type Coat Protein (Stonehouse, 1993). Higher concentrations of the Coat Protein are needed to induce capsid assembly than for the wild-type sequence. However, Armored RNA™ assembled in vivo in the presence of these mutant Coat Proteins may be more efficient for RNA delivery.

EXAMPLE XIX

Production of RNA to Construct an Affinity Column

The need for RNA extends to producing columns for the affinity purification of proteins which bind to specific RNA sequences. Such proteins are involved in the regulation of translation and in RNA turnover. Armored RNA™ technology may be used to produce large quantities of a specific RNA sequence. The reRNA would be purified from the Armored RNA™ particles. The reRNA could be covalenftly conjugated to a solid phase resin. Alternatively, a more generic resin may be developed in which Coat Protein was covalently bound to the resin. The reRNA could be immobilized to the resin by its binding to the Coat Protein through the Operator sequence. The non-phage sequence in the reRNA would then be used to pull out proteins which specifically recognize it In another format, the protein-reRNA binding could occur in solution, to better mimic the actual interaction and then the free reRNA and the protein-reRNA complexes would be concentrated using a Coat Protein column. The column may be subjected to ribonuclease to release the proteins which bound to the reRNA. These proteins may then be characterized by gel electrophoresis or the material eluted from the column may be injected into animals such as mice and rabbits to produce antibodies. Once antibodies are produced, then cDNA expression libraries may be screened for the gene responsible for the protein binding to the RNA.

EXAMPLE XX

Packaging of Capped mRNA In Vivo

Using Armored RNA™ technology, mRNA may be capped and packaged in E. coli. The enzyme RNA guanyltransferase is responsible for capping the 5' terminus of an mRNA using GTP and S-adenosylmethionine (SAM) as substrates. RNA guanyltransferase has been cloned and expressed in E. coli in an active form (Cong, 1995). The RNA guanyltransferase may be co-expressed with the RNA to be capped and to be packaged as an Armored RNA™ particle. In the preferred embodiment, the non-phage RNA would be positioned at the 5' end of the reRNA.

EXAMPLE XXI

Encapsulation as a Method For Producing Nuclease-Resistant RNA

"Caging," or encapsulation of RNA makes an RNA not accessible to an RNase-containing solution. Encapsidation of RNA by viral proteins is an example of microencapsulation. Microencapsulation is a process whereby a molecule (in this case RNA) is surrounded by a structure that denies access to the internalized molecule. Microencapsulation confers nuclease-resistance upon RNA by sequestering the RNA from the nuclease-contaminated environment. In addition to viral protein encapsidation, the most common methods of microencapsulation are internalization in liposomes and inclusion in polymer matrices. Viral protein encapsidation has proven capable of providing nuclease-resistant RNAs (see Armored RNA above). Liposomes and polymer matrices partition molecules in a manner that is analogous to protein encapsidation, thus they are expected to perform equally well in protecting internalized RNA standards.

1. Liposomes

The formation of liposomes occurs spontaneously when lipids are dispersed in aqueous solutions. Reagents that are present in the aqueous solution are encapsulated during liposome formation, providing a relatively simple method for microencapsulating pharmaceuticals, cells, proteins, and nucleic acids. Several methods exist for producing liposomes (Vemuri 1995). The best characterized of these involves adding an excess volume of reagent-containing aqueous buffer to a round-bottomed flask in which a lipid solution had been lyophilized. The addition of the aqueous solution first dissolves the lipids and then causes them to form liposomes that engulf portions of the aqueous solution. This effectively produces liposome-encapsulated reagents that can be purified, quantified, stored, and eventually used in diagnostic assays.

2. Polymer Matrices

A variety of monomers can be converted to polymeric microspheres by dropwise dispersion into a solution that encourages polymerization. Molecules dissolved in either the monomer solution or the solution in which the polymerization is occurring will be trapped in the microspheres. Purification of the microspheres provides trapped reagents that are inaccessible to macromolecules in the surrounding solution.

An illustration of how to produce reagent-containing microspheres comes from a study on the microencapsulation of rotavirus in alginate/spermine matrices (Offit 1994). A rotavirus suspension mixed with sodium alginate (0.68 mM) was dispersed as 5 µm droplets into 0.55 mM spermine hydrochloride. The mixture was centrifuged at 600× g and washed several times to purify the rotavirus containing microspheres. Analysis of the microspheres revealed that the rotavirus were contained within the polymer matrix, and that upon release, they were still infectious. These two points are important as it reveals that microspheres sequester molecules from the surrounding solution and that the internalized molecule is being maintained in its native state. Microencapsulation of an RNA standard could be done by replacing the rotavirus suspension with an RNA solution.

A single, general method can be employed for incorporating microencapsulated RNAs into a diagnostic assay. RNAs possessing domains sufficient for detection (primer binding or hybridization sites) would be encapsulated by one of the methods mentioned above. The encapsulated RNA would be purified, quantified, and stored for future use. For diagnostics, the microencapsulated standard would be diluted and aliquoted into the samples at an appropriate step. If the standard RNA isolation procedure in the diagnostic protocol does not adequately release the standard, or if the standard is added after the isolation step, then heating the sample to 90° C. for 2-5 minutes will be sufficient for release from most microcapsules. The RNA detection portion of the assay could then be performed.

EXAMPLE XXII

Noncovalently Bound RNA as a Nuclease-Resistant Standard

RNAs are bound with relatively high affinity by a variety of molecules. In many cases, the RNA can be completely coated by the interacting molecules. There are examples whereby the presence of the bound molecules renders the RNA resistant to nuclease degradation. This general scheme provides an additional method for generating nuclease-resistant RNA standards.

There are a variety of proteins, nucleic acids, and small molecules that bind RNA. Footprinting experiments with HIV-1 nucleocapsid protein (Allen 1996) and the regA protein of T4 (Winter et al. 1987) show that bound molecules can render an RNA resistant to nucleases. Proteins and small molecules that bind RNA cooperatively often coat large regions of the polymers. Examples include the T4 gene 32 protein (von Hippel 1982), MS2/R17 coat protein (Witherall 1990), and the small molecules spermine and spermidine (McMahon 1982). The combination of cooperative binding and nuclease occlusion can effectively protect large domains of RNAs from degradation (Allen 1996) making them ideal nuclease-resistant standards. Poly-L-lysine is able to protect the natural double-stranded RNAs interferon inducers, larifan and ridostin, from ribonucleases in human blood serum. The free interferon inducers in serum completely lost their activity after 4 hour incubation in serum. The protective activity of poly-L-lysine increased in parallel with the increase in its molecular weight. The protective activity was maximal with material of 12,300+/−1,000 Daltons (Surzhik et al., 1993).

Cetyltrimethylammonium bromide (CTAB) is a cationic detergent which has been long used for the isolation of nucleic acids by virtue of its ability to bind to and precipitate nucleic aids but not protein (Jones, 1953; Jones, 1963). The positively charged head groups can bind to the negatively charged backbone of the RNA, protecting the RNA from ribonuclease. Experiments by Winkler and Kessler (unpublished) demonstrate that 20 mM CTAB protects as much as S micrograms RNA from digestion by RNase A and RNase T1. If 0.5% Triton X-100 is added to the CTAB/RNA solution, the CTAB is solubilized by the Triton X-100 and the protective action is reversed.

Similarly, nucleic acids afford nuclease protection by directly interacting with RNA (Weigand 1975). Short (ten nucleotides), random sequence nucleic acids can be hybridized to an RNA, effectively coating the molecule. Incubation in a sample that includes RNases would not be detrimental, as the RNA would be bound by the randomers, and thus protected. If an amplification scheme is used for detection, the short randomers could serve as primers for reverse transcriptase.

A general scheme can be devised by one of skill for employing any of the noncovalently bound RNAs as standards. An RNA with sequences for primer binding (for RT-PCR, NASBA, or 3SR) or probe hybridization (branched DNA assay or DiGene's antibody based assay) can be prebound by any of the RNA binding molecules mentioned in the preceding paragraphs. This bound RNA would be accurately quantified and stored for future use. The bound RNA would be diluted, and aliquoted into samples, either before or after RNA purification. Prior to amplification or hybridization (depending on the detection protocol), the sample would be heated to 90° C. to release the RNA standard. The amplification or hybridization could then be performed, producing a signal for detection.

EXAMPLE XXIII

RNA Bound by gp32 is Nuclease-Resistant

An RNA bound by the protein encoded by gene 32 of the bacteriophage T4 (gp32) was used to demonstrate the effectiveness of noncovalent binding methodology for making RNA standards. gp32 is known to bind RNA and ssDNA cooperatively (von Hippel 1982). The purified protein (~1 μM) was mixed with a radiolabeled RNA target (~100 nM) for five minutes at room temperature in a buffer consisting of 50 mM HEPES pH 7.4, 200 mM NaCl, and 2.5 mM $MgCl_2$. By gel shift assay, approximately 50% of the RNA molecules were bound by the protein. A tenth volume of goat serum was added to the coated RNA and the mixture was incubated at 25° C. for ten minutes. The RNA was separated via PAGE and detected by autoradiography. The amount of intact RNA was greater than an identical RNA sample that lacked the protein. This illustrates that the presence of gp32 protects RNA from serum-mediated degradation and argues that the concept of nuclease protection generated by cooperatively bound molecules is valid.

A sample of the same RNA used above was bound by gp32 using the described procedure. This sample was heated to 95° C. for 2 minutes and then reverse transcribed by AMV reverse transcriptase using a primer specific to the 3' end of the RNA. The resulting cDNA was serially diluted and the various dilutions were used to initiate a standard PCR reaction using primers specific to the RNA standard. The PCR products were analyzed by gel electrophoresis. The dilution at which product was first observed was the same for the gp32-bound RNA as for an unbound RNA subjected to the same procedure. This indicates that the T4 protein does not affect the capacity of RT to use the RNA as a template, nor does it subsequently affect the PCR reaction. Protein-coated RNAs have also been diluted into a 10% serum solution for fifteen minutes and then applied to an RT-PCR experiment. Products of the appropriate size were generated, providing evidence that cooperative binding of an RNA is a useful method for producing stable RT-PCR controls.

EXAMPLE XXIV

Protection of RNA through Chemical Modification

One method for making RNAs resistant to enzyme-mediated degradation is to chemically alter the RNA so that the mechanism for degradation is blocked or so that RNases no longer recognize the molecule as RNA. Such alterations can be made to nucleotides prior to their incorporation into RNA or to RNA after it has been formed. Ribose (Piecken 1991) and phosphate (Black 1972) modifications have been shown to enhance RNA stability in the presence of nucleases. Modifications of the 2' hydroxyl and internucleotide phosphate confers nuclease resistance by altering chemical groups that are necessary for the degradation mechanism employed by ribonucleases (Heidenreich 1993). Another method could be accomplished by chemically adding molecules (e.g., carbohydrates) to the RNA standard. These chemical groups could be removed enzymatically or chemically during the detection protocol to allow for reverse transcription. Provided that they are templates for the reverse transcription or hybridization protocols used in nucleic acid detection schemes, chemically modified RNAs will be ideally suited as RNA standards as they are considerably more stable than non-modified RNA.

The general scheme for using chemically modified RNAs as standards in diagnostic assays is to simply replace the current RNA standards with modified RNAs possessing the same sequence. Transcribe the DNA template encoding the RNA standard using T7 RNA polymerase, replacing the standard NTPs with ribose or phosphate modified NTPs. The resulting full-length RNA can be purified, quantified and stored for future use. At the time of the assay, the modified RNA standard can be appropriately diluted, aliquoted into sample either before or after RNA purification, and then co-detected with the sample RNA.

EXAMPLE XXV

Protection of RNA With 2' Fluoro CTP and UTP

To test the usefulness of modified RNAs as standards, nucleotide analogs were incorporated into transcripts and compared to unmodified RNAs. 2' fluoro CTP and UTP were incorporated into transcripts by 0.5 units/μl of 17 RNA polymerase in transcription buffer (40 mM Tris pH 8.0, 20 mM NaCl , 6 MM $MgCl_2$, 6 mM $MnCl_2$, 2 mM spermidine, 10 mM DTT). Ten picomoles of modified and unmodified RNA were reverse transcribed by AMV reverse transcriptase. A dilution series of the resulting cDNAs were amplified by PCR. The products were separated via PAGE and analyzed by ethidium bromide staining. Both the modified and unmodified RNA samples generated identical results, indicating that the modifications have no effect on the quantification of the RNAs by RT-PCR The modified RNAs were incubated in serum for one hour and the products were size-separated by PAGE. No degradation of the modified RNAs was apparent, while an unmodified RNA of the same sequence was completely degraded. Thus, the modified RNAs would be far superior to unmodified RNA as they could be added earlier in the diagnostic protocol (providing a better internal standard) and they would be more stable during storage.

The ultimate test of the modified RNA is to show its compatibility with an existing diagnostic assay. A template encoding the sequence of the standard for the Amplicor HIV Monitor™ assay was transcribed with 2'F CTP and UTP as above. A series of dilutions of the 2' F modified RNA was applied to the Amplicor HIV Monitor™ test. The modified standard produced a signal in a concentration dependent fashion, providing evidence that the modified RNA was being reverse transcribed and that the resulting cDNA was being PCR amplified. The modified RNA standard was then compared to an unmodified RNA. Both standards produced approximately equal signals when introduced after the lysis step of the detection protocol, but when the two RNAs were incubated in plasma for fifteen minutes prior to incorporation into the detection protocol, the signal produced by the unmodified RNA was indistinguishable from background whereas the modified RNA produced signals that were nearly equivalent to that observed when the RNA was not preincubated in plasma This latter observation points to the obvious advantage of the modified RNA standard, namely that the RNA can be added earlier in the protocol (prior to sample lysis) providing a better control for the overall experiment. Additionally, nuclease-resistance will be beneficial during storage, as the likelihood of degradation prior to assaying will be greatly diminished.

Phosphate modified nucleotides, in the form of α-thiols of CTP and UTP, were incorporated into transcripts by 17 RNA polymerase as the 2'F above. The resulting RNAs were templates for reverse transcriptase. PCR analysis revealed that the modified RNAs were converted to cDNAs as efficiently as unmodified RNAs.

Although the work described used only modified pyrimidines, modified purines can also be incorporated into RNA [Aurup et al. (1994)]. This might be important in a case where a high concentration of a purine-specific nuclease is present in a group of samples. Because a variety of nucleotide analogs exist that can be incorporated, RNAs can be tailored for different storage and reaction conditions to ensure optimum stability and assay efficiency.

EXAMPLE XXVI

Assay for Ribonuclease Protection

To test a potential ribonuclease-resistant construct for ribonuclease resistance, a protected RNA construct is incubated with ribonuclease, such as Ribonuclease 1 or Ribonuclease A, at 37° C. for several different time points, 15 minutes, 30 minutes, 1 hour, 2 hours. During the same experiment, naked RNA isolated from the same Armored RNA construct is also incubated with the ribonuclease. After each time period, the ribonuclease is inactivated by phenol extraction. The phenol also strips the coat protein from the RNA in an Armored RNA construct. After phenol extraction, the RNA is ethanol precipitated. The isolated RNA is fractionated on a denaturing formaldehyde agarose gel, stained with ethidium bromide and assessed for degradation. Degradation is assessed by comparing the ribonuclease treated samples to RNA which was not ribonuclease treated.

Alternatively, instead of analyzing the RNA by gel electrophoresis, a sample can be subjected to competitive RT-PCR to obtain a more accurate, quantitative result. The use of PCR also has the advantage of detecting small amounts of material.

EXAMPLE XXVII

Standard Steps in Using Any RNase Resistant Standard

Many assays employing RNase resistant standards will have the same basic format as the Amplicor HIV Monitors assay described above. In such a kit, known amounts of RNase resistant standard is added to the RNA sample. The sample RNA and the RNA standard (eg., Armored RNA™ chemically modified RNA or any other ribonuclease protected RNA) are co-purified from plasma or from cells. For some assays, the sample RNA will already have been purified. In such cases, the RNase resistant standard may be added directly to the sample RNA. The mixture can then be heated for 5 minutes, 70° C. to strip off a protein coat, or any other molecule that confers ribonuclease resistance, or treated in any other manner necessary.

After the RNA has been purified or heated, the sample RNA and the standard RNA are reverse transcribed and then co-amplified by PCR. If the standard RNA has a deletion or insertion, then the PCR products may be fractionated on a gel. The PCR product generated from the RNA standard will have a different mobility than the PCR product derived from the sample RNA. A standard curve can be generated plotting the concentration of RNA standard and the amount of PCR product generated from the standard. The concentration of the sample RNA is derived by interpolation within the linear range of the curve.

In the HIV Monitor™ assay, the RNA standard has a 26 nucleotide substitution compared to the sample RNA sequence. Quantification of the PCR products are derived by using immobilized oligonucleotides to specifically capture the PCR products by hybridizing to the test PCR product or the standard PCR product. The PCR products are 5' biotinylated. The captured PCR products are detected calorimetrically using streptavidin horseradish peroxidase. Once again, the concentration of the unknown RNA sample is calculated using the signal produced by the known concentration of the standard RNA.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ackerman, "Frequency of Morphological Phase Descriptions," *Arch. Virol.,* 124:201-209, 1992.

Allen, Collins, Brown, Hostomsky, Gold, "A Specific RNA Structural Motif Mediates High Affinity Binding by the HIV-1 Nucleocapsid Protein (Ncp-7)," *Virology,* 225: 306-15, 1996.

Argetsinger, Gussin, "Intact ribonucleic acid from defective particles of bacteriophage R17," *J. Mol. Biol.,* 21:421-434, 1966.

Aurup, Williams, Eckstein, "2'-Flouro- and 2'-amino-2'-deoxynucleoside 5'-triphosphates as substrates for T7 RNA Polymerase," *Biochemistry,* 31:9636-41, 1992.

Aurup, Siebert, Benseler, Williams, Eckstein, "Translation of 2'-modified mRNA in vitro and in vivo," *Nuc. Acids Res.,* 22:4963-68, 1994.

Barry, Dower, Johnston, "Toward cell-targeting gene therapy vectors: selection of cell-binding peptides from random peptide-presenting phage libraries," *Nature Medicine,* 2:299-305, 1996.

Beckett, Wu, Uhlenbeck, "Roles of the Operator and non-Operator RNA sequences in bacteriophage R17 capsid assembly," *J. Mol. Biol.,* 204:939-947, 1988.

Birnboim, "A rapid alkaline extraction method for the isolation of plasmid DNA," *Methods Enzymol.,* 100:243-255.

Black, Eckstein, DeClercq, Merigan, "Studies on the Toxicity and Antiviral Activity of Various Polynucleotides," *Antimicrob. Agents Chemotherap.,* 3:198-206, 1972.

Chomczynski, Sacchi, "Single-step method of RNA isolation by acid guanidinium thiocyanate-phenol-chloroform extraction," *Anal. Biochem.,* 162:156-159, 1987.

Collins, Zayati, Detmer, Daly, Kolberg, Cha, Irvine, Tucker, Urdea, "Preparation and characterization of RNA standards for use in quantitative branched DNA hybridization assays," *Anal. Biochem.,* 226:120-129, 1995.

Cong, Shuman, "Mutational analysis of mRNA capping enzyme identifies amino acids involved in GTP binding, enzyme-guanylate formation, and GMP transfer to RNA," *Mol. Cell. Biol.,* 15:6222-6231, 1995.

Conry, LoBuglio, Wright, Sumerel, Pike, Johanning, Benjamin, Lu, Curiel, "Characterization of a messenger RNA polynucleotide vaccine vector," *Cancer Res.,* 55:1397-1400, 1995.

Dhaese, Lenaerts, Gielen, van Montagu, "Complete amino acid sequence of the Coat Protein of the *Pseudomonas aeruginosa* RNA bacteriophage PP7," *Biochem. Biophys. Res. Commun.,* 94:1394-1400, 1980.

Dhaese, Vandekerchhove, van Montagu, "The primary structure of the Coat Protein of the broad-host-range RNA bacteriophage PRR1," 94:375-386, 1979.

Douglas, Rogers, Rosenfeld, Michael, Feng, Curiel, "Targeted gene delivery by tropism-modified adenoviral vectors," *Nature Biotech.,* 14: 1574-1578, 1996.

Dwarki, Malone, Venna, "Cationic liposome-mediated RNA transfection," *Methods Enzymol.,* 217:644654, 1993.

Elroy-Stein, Fuerst, Moss, "Cap-independent translation of mRNA conferred by encephalomyocarditis virus 5' sequence improves the performance of the vaccinia virus/bacteriophage T7 hybrid expression system," *Proc. Natl. Acad. Sci. USA,* 86: 6126-6130, 1989.

Essex, "The HIV-1 vaccine dilemma: Lessons from the cat," *J. NIH Res.,* 7:37-42, 1995.

Ferré-D'Amaré, Doudna, "Use of cis- and trans-ribozymes to remove 5' and 3' heterogeneities from milligrams of in vitro transcribed RNA," *Nucleic Acid Res.,* 24:977-978, 1996.

Frolov, Hoffman, Prágai, Dryga, Huang, Schlesinger, Rice, "Alphavirus-based expression vectors: Strategies and applications," *Proc. Natl. Acad. Sci. USA,* 93:11371-11377,1996.

Gallie, Sleat, Watts, Turner, Wilson, "In vivo uncoating and efficient expression of foreign mRNAs packaged in TMV-like particles," *Science,* 236: 1122-1124, 1987.

Golmohammadi, Valegård, Fridborg, Liljas, "The refined structure of bacteriophage MS2 at 2.8 Å resolution," *J. Mol. Biol.,* 234:620-639, 1993.

Griffiths, Potter, Eperon, "Stereospecificity of nucleases towards phosphorothioate-substituted RNA: stereochemistry of transcription by T7 RNA polymerase," *Nucl. Acids Res.,* 15:4145-62, 1987.

Hart, Knight, Harbottle, Mistry, Hunger, Cutler, Williamson, Coutelle, "Cell binding and internalization by filamentous phage displaying a cyclic Arg-Gly-Asp-containing peptide," *J. Biol. Chem.,* 269:12468-12474, 1994.

Heidenreich, Pieken, Eckstein, "Chemically Modified RNA: approaches and applications," *FASEB J.,* 7:90-6, 1993.

Heisenberg, "Formation of defective bacteriophage particles by fr amber mutants," *J. Mol. Biol.,* 17:136–144, 1966.

Hughes, "Creation of deletion, insertion and substitution mutations using a single pair of primers and PCR™," *BioTechniques,* 20:188–196, 1996.

Hwang, Roberts, Wilson, "Assembly of tobacco mosaic virus and TMV-like pseudovirus particles in *Escherichia coli,*" *Arch. Virol., Suppl.* 9:543–558, 1994. ("Hwang 1994a")

Hwang, Roberts, Wilson, "Expression of tobacco mosaic virus coat protein and assembly of pseudovirus particles in *Escherichia coli,*" *Proc. Natl. Acad. Sci. USA,* 91:9067–9071, 1994. ("Hwang 1994b")

Jones, "The isolation of bacterial nucleic acids using cetyltrimethylammonium bromide (centavlon)," *Biochemica ET Biophysica ACTA,* 10: 607–612, 1953.

Jones, "Use of alkyltrimethylammonium bromides for the isolation of ribo- and deoxyribo-nucleic acids," *Nature,* 199: 280–282, 1963.

Jupin, Sleat, Watkins, Wilson, "Direct recovery of in vitro transcripts in a protected form suitable for prolonged storage and shipment at ambient temperatures," *Nucl. Acids Res.,* 17: 815, 1989.

Lapham, Crothers, "RNase H cleavage for processing of in vitro transcribed RNA for NMR studies and RNA ligation," RNA, 2:289–296, 1996.

LeCuyer, Behlen, Uhlenbeck, "Mutants of the bacteriophage MS2 Coat Protein that alter its cooperative binding to RNA," *Biochemistry,* 34:10600–10606, 1995.

Lu, Andrieu, "Use of the human immunodeficiency virus virion as a universal standard for viral RNA quantification by reverse transcription-linked polymerase chain reaction," *J. Infect. Dis.,* 167:1498–1499, 1993.

Lu, Benjamin, Kim, Conry, Curiel, "Optimization of methods to achieve mRNA-mediated transfection of tumor cells in vitro and in vivo employing cationic liposome vectors," *Cancer Gene Ther.,* 1:245–252, 1994.

Mastico, Talbot, Stockley, "Multiple presentation of foreign peptides on the surface of an RNA-free spherical bacteriophage capsid," *J. Gen. Virol.,* 74: 541–548, 1993.

McMahon, Erdmann, "Binding of Spermidine to Transfer Nucleic Acid," *Biochemistry,* 21:5280–88, 1982.

Mulder, McKinney, Christopherson, Sninsky, Greenfield, Kwok, "Rapid and simple PCR™ assay for quantitation of human immunodeficiency virus type 1 RNA in plasma: application to acute retroviral infection," *J. Clin. Microbiol.,* 32:292–300, 1994.

Offit, Khoury, Moser, Clark, Kim, Speaker, "Enhancement of Rotavirus Immunogenicity by Microencapsulation," Virology 203, 134–143, 1994.

Pachl, Todd, Kern, Sheridan, Fong, Stempien, Hoo, Besemer, Yeghiazarian, Irvin, Kolberg, Kokka, Neuwald, Urdea, "Rapid and precise quantification of HIV-1 RNA in plasma using a branched DNA signal amplification assay," *J. Acquir. Immune Deficiency. Syndr.,* 8:446–454, 1995.

Pearson, Chen, Gaynor, Sigman, "Footprinting RNA-protein complexes following gel retardation assays: Application to the R-17-procoat-RNA and tat-TAR interactions," *Nucl. Acids Res.,* 22:2255–2263, 1994.

Piatak Jr., Luk, Williams, Lifson, "Quantitative competitive polymerase chain reaction for accurate quantitation of HIV DNA and RNA," *BioTechniques,* 14:70–79, 1993.

Pickett, Peabody, "Encapsidation of heterologous RNAs by bacteriophage MS2 Coat Protein," *Nucl. Acids Res.,* 21:4621–4626, 1993.

Piecken, Olsen, Benseler, Aurup, Eckstein, "Kinetic Characterization of Ribonuclease-Resistant 2'-modified Hammerhead Ribozymes," *Science,* 253:314–17,1991.

Qiao, Qiao, Mindich, "Interference with bacteriophage (6 genomic RNA packaging by hairpin structures," *J. Virol.,* 69:5502–5505, 1995.

Schneeberger, Zeillinger, "PCR™-mediated synthesis of exogenous competitors for quantitative RT-PCR™," *BioTechniques,* 20:360–362, 1996.

Shaklee, "Negative-strand RNA replication by Q-beta and MS2 positive-strand RNA phage Replicases," *Virology,* 178:340–343, 1990.

Shiba, Suzuki, "Localization of A protein in the RNA-A protein complex of RNA phage 1) MS2," *Biochem. Biophys. Acta,* 654:249–255, 1981.

Simmonds, Alberti, Alter et al., "A proposed system for the nomenclature of hepatitis C virus genotypes," *Hepatology,* 19:1321–1324, 1994.

Stiehin, Kronenberg, Rosenblatt, Bryson, Merigan, UCLA conference. "Interferon: immunology and clinical significance," *Ann. Intern. Med.,* 96: 80–93, 1982.

Stockley, Stonehouse, Valegård, "Molecular mechanism of RNA phage morphogenesis," *Int. J. Biochem.,* 26:1249–1260, 1994.

Stonehouse, Stockley, "Effects of amino acid substitution on the thermal stability of MS2 capsids lacking genomic RNA," *FEBS Lett.,* 334: 355–359, 1993.

Surzhik, Duks, Diatlova, Glazunov, Feldmane, Timkovskii, "Interrelationship between the chain length of poly-L-lysine and the degree of protection of polyribonucleotide interferon inducers from human blood nucleases," *Antibiot. Khimioter,* 38(7): 21–25, 1993.

van Doorn, Kleter, Stuyver, Maertens, Brouwer, Schalm, Heijtink, Quint, "Analysis of hepatitis C virus genotypes by a line probe assay and correlation with antibody profiles," *J. Hepatology,* 21:122–129, 1994.

van Gemen, van Beuningen, Nabbe, van Strijp, Jurriaans, Lens, Kievits, "A one-tube quantitative HIV-1 RNA NASBA nucleic acid amplification assay using electrochemiluminescent (ECL) labeled probes," *J. Virol. Methods,* 49:157–168, 1994.

Vemuri, Rhodes, "Preparation and Characterization of Liposomes as Therapeutic Delivery Systems: A Review," *Pharmaceutica Acta Helvetiae,* 70: 95–111, 1995.

von Hippel, Kowalczykowski, Lonberg, Newport, Paul, Stormo, Gold, In: *Bacteriophage T4,* eds. Mathews, Kutter, Mosig, Berget, pp. 202–207, 1982.

Weigand et al., "Specificity of the S1 Nuclease from *Aspergillus Oryzae,*" *J. Biol, Chem.,* 250:8848–55, 1975.

Wilson, Hwang-Lee, "RNA packaging system," U.S. Pat. No. 5,443,969. Issued Aug. 22, 1995.

Winter, Morrissey, Gauss, Gold, Hsu, Karam, "Bacteriophage T4 regA protein binds to mRNAs and prevents translation initiation," *Proc. Natl. Acad. Sci. USA,* 84:7822–26, 1987.

Witherall, Wu, Uhlenbeck, "Cooperative Binding of the R17 Coat Protein to RNA," *Biochemistry,* 29:11051–57, 1990.

Witherell, Gott, Uhlenbeck, "Specific interaction between RNA phage Coat Proteins and RNA," *Proc. Nuc. Acid Res. Molec. Biol.,* 40:185–220,1991.

Witherell, Wu, Uhlenbeck, "Cooperative binding of R17 Coat Protein to RNA," *Biochem.,* 29:11051–11057, 1990.

Young, Resnick, Myers, "Detection of Hepatitis C Virus RNA by a combined reverse transcription-polymerase chain reaction assay," *J. Clin. Microbiol.,* 31:88–886, 1993.

Zhoa, Fox, Olson, Baker, Young, "In vitro assembly of cowpea chlorotic mottle virus from coat protein expressed in *Escherichia coli* and in vitro-transcribed viral cDNA," *Virology,* 207:486494, 1995.

What is claimed is:

1. A method of encapsidating a nucleic acid in a viral coat protein comprising:
    obtaining a nucleic acid segment, wherein the nucleic acid segment comprises a sequence adapted for use as a standard in detection and/or quantification of a nucleic acid;
    obtaining viral coat protein; and
    placing the nucleic acid segment and the viral coat protein together under conditions causing the nucleic acid segment to become encapsidated in the viral coat protein, and
    employing the nucleic acid segment encapsidated in the viral coat protein as a detection and/or quantification standard in an assay for detecting or quantifying a nucleic acid.

2. The method of claim 1, wherein the conditions causing the nucleic acid segment to become encapsidated in the viral coat protein are further defined as in vitro conditions.

3. The method of claim 1, wherein the nucleic acid segment is RNA.

4. The method of claim 1, wherein the viral coat protein is a bacteriophage viral coat protein.

5. The method of claim 4, wherein the bacteriophage viral coat protein is of an *E. coli* bacteriophage of genetic subclass A or B.

6. The method of claim 5, wherein the bacteriophage viral coat protein is of an *E. coil* bacteriophage of genetic subclass A.

7. The method of claim 4, wherein the bacteriophage viral coat protein is of an *E. coli* bacteriophage in serological group I; II, III, or IV.

8. The method of claim 7, wherein the bacteriophage viral coat protein is of an *E. coli* bacteriophage in serological group I.

9. The method of claim 4, wherein the bacteriophage viral coat protein is of an MS21R17 bacteriophage.

10. The method of claim 4, wherein the bacteriophage viral coat protein is of a Pseudomonos aeruginosa RNA bacteriophage.

11. The method of claim 4, wherein the bacteriophage viral coat protein is of a filamentous bacteriophage.

12. The method of claim 1, wherein the viral coat protein is a viral coat protein of a plant or animal virus.

13. The method of claim 12, wherein the viral coat protein is a viral coat protein of a tobacco mosaic virus, a feline immunodeficiency virus, or a Rous sarcoma virus.

14. The method of claim 13, wherein the viral coat protein is a viral coat protein of a tobacco mosaic virus.

15. The method of claim 1, wherein the nucleic acid segment comprises a non-bacteriophage sequence.

16. The method of claim 15, wherein the non-bacteriophage sequence is a viral sequence.

17. The method of claim 15, wherein the non-bacteriophage sequence is a sequence adapted for use as a standard in detection and/or quantification of a nucleic acid.

18. The method of claim 17, wherein the non-bacteriophage sequence is a sequence adapted for use in detection and/or quantification of a nucleic acid of diagnostic value.

19. The method of claim 18, wherein the non-bacteriophage sequence is a sequence adapted for use in detection and/or quantification of a virus.

20. The method of claim 19, wherein the virus is an RNA virus.

21. The method of claim 20, wherein the non-bacteriophage sequence is a sequence adapted for use as a standard in detection and/or quantification of HIV-1, HIV-2, HCV, HTLV-1, HTLV-2, hepatitis G, an enterovirus, or a blood-borne pathogen.

22. The method of claim 21, wherein the non-bacteriophage sequence is a sequence adapted for use as a standard in detection and/or quantification of HIV-1.

23. The method of claim 22, wherein the non-bacteriophage sequence adapted for use as a standard in detection and/or quantification of HLV-1 comprises a modified HIV-1 sequence.

24. The method of claim 21, wherein the non-bacteriophage sequence is a sequence adapted for use as a standard in detection and/or quantification of HCV.

25. The method of claim 24, wherein the non-bacteriophage sequence adapted for use as a standard in detection and/or quantification of HCV comprises a modified HCV sequence.

26. The method of claim 15, wherein the nucleic acid segment further comprises a bacteriophage sequence.

27. The method of claim 26, wherein the bacteriophage sequence is a sequence from an E. coli bacteriophage of genetic subclass A.

28. The method of claim 4, wherein the nucleic acid segment comprises at least one operator sequence and a non-bacteriophage sequence.

29. The method of claim 1, wherein the nucleic acid segment encapsidated in the viral coat protein is used as an internal nucleic acid standard.

30. The method of claim 1, wherein the nucleic acid segment encapsidated in the viral coat protein is used as an external nucleic acid standard.

31. The method of claim 1, wherein the nucleic acid segment encapsidated in the viral coat protein is used as a positive control nucleic acid standard.

32. The method of claim 15, wherein the non-bacteriophage sequence is used for the detection or quantification of an mRNA.

33. The method of claim 32, wherein the mRNA is cellular mRNA.

34. The method of claim 32, wherein the mRNA is a cytokine, a cell cycle gene, or an oncogene mLRNA.

* * * * *

UNITED STATES PATENT AND TRADEMARK OFFICE
CERTIFICATE OF CORRECTION

| | | |
|---|---|---|
| PATENT NO. | : 7,033,749 B2 | Page 1 of 1 |
| APPLICATION NO. | : 10/120013 | |
| DATED | : April 25, 2006 | |
| INVENTOR(S) | : Brittan L. Pasloske et al. | |

It is certified that error appears in the above-identified patent and that said Letters Patent is hereby corrected as shown below:

In claim 7, column 55, line 32, delete ";" and insert --,-- therefor.

In claim 9, column 55, line 37, delete "MS21R17" and insert --MS2/R17-- therefor.

In claim 10, column 55, line 39, delete "Pseudomonos aeruginosa" and insert --*Pseudomonas aeruginosa*-- therefor.

In claim 23, column 56, line 19, delete "HLV-1" and insert --HIV-1-- therefor.

In claim 27, column 56, line 31, delete "E. coli" and insert --*E. coli*-- therefor.

In claim 34, column 56, line 51, delete "mLRNA" and insert --mRNA-- therefor.

Signed and Sealed this

Fifteenth Day of August, 2006

JON W. DUDAS
*Director of the United States Patent and Trademark Office*